US007275823B2

United States Patent
Fukuma et al.

(10) Patent No.: US 7,275,823 B2
(45) Date of Patent: Oct. 2, 2007

(54) OPTOMETRIC DEVICE

(75) Inventors: Yasufumi Fukuma, Tokyo (JP); Kohji Nishio, Tokyo (JP); Takefumi Hayashi, Tokyo (JP); Noriyuki Nagai, Tokyo (JP); Yasuo Kato, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 609 days.

(21) Appl. No.: 10/495,475

(22) PCT Filed: Nov. 13, 2002

(86) PCT No.: PCT/JP02/11848

§ 371 (c)(1),
(2), (4) Date: May 13, 2004

(87) PCT Pub. No.: WO03/041571

PCT Pub. Date: May 22, 2003

(65) Prior Publication Data

US 2005/0018132 A1    Jan. 27, 2005

(30) Foreign Application Priority Data

Nov. 13, 2001   (JP)   ............................. 2001-347988

(51) Int. Cl.
*A61B 3/10*   (2006.01)
(52) U.S. Cl. .................................................... 351/205
(58) Field of Classification Search ......... 351/200–246
See application file for complete search history.

(56) References Cited

U.S. PATENT DOCUMENTS

| 5,231,430 | A | * | 7/1993 | Kohayakawa | ............... 351/243 |
| 5,502,519 | A | * | 3/1996 | Hosoi | ......................... 351/204 |
| 5,555,039 | A | * | 9/1996 | Iki et al. | ..................... 351/205 |
| 5,629,748 | A | | 5/1997 | Hayashi et al. | ............. 351/232 |
| 6,145,990 | A | * | 11/2000 | Uchida | ....................... 351/221 |

FOREIGN PATENT DOCUMENTS

| JP | 01-164350 | | 6/1989 |
| JP | 05-176896 | A | 7/1993 |
| JP | 07-194540 | A | 8/1995 |
| JP | 09-122074 | A | 5/1997 |
| JP | 2694915 | | 9/1997 |
| JP | 2693772 | B2 | 12/1997 |
| JP | 2000-083900 | | 3/2000 |

OTHER PUBLICATIONS

Korean Intellectual Property Office, Notice of Preliminary Rejection, Korean Patent Application No. 10-2004-7006284, Jan. 18, 2006.
Korean Intellectual Property Office, Notice of Preliminary Rejection, Korean Patent Application No. 10-2004-7006284, Aug. 14, 2006.
Patent Office of the People's Republic of China, First Office Action, Chinese Patent Application No. 02822367.5, 2007.

* cited by examiner

*Primary Examiner*—M. Hasan
(74) *Attorney, Agent, or Firm*—Chapman and Cutler LLP

(57) ABSTRACT

In an optometric apparatus of the present invention, optometric apparatus bodies 5*l* and 5*r* independently driven in right-and-left and up-and-down directions for optometry of an examinee 4, respectively, are provided on both sides of a face receiving device 6.

19 Claims, 29 Drawing Sheets

☐ is a standard examination routine, ⋮ ⋮ is a setting file and means selection.

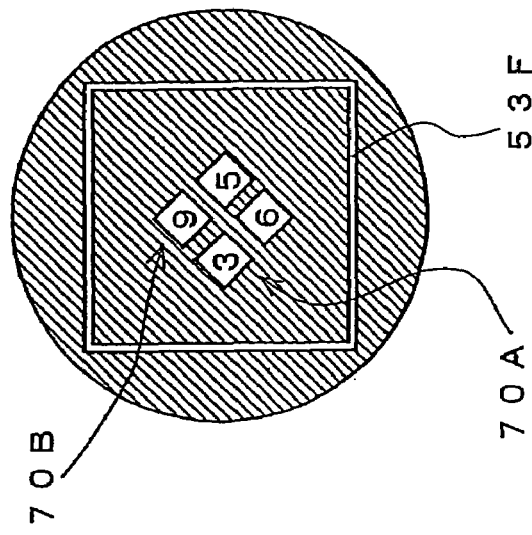
FIG.16(a) Left eye
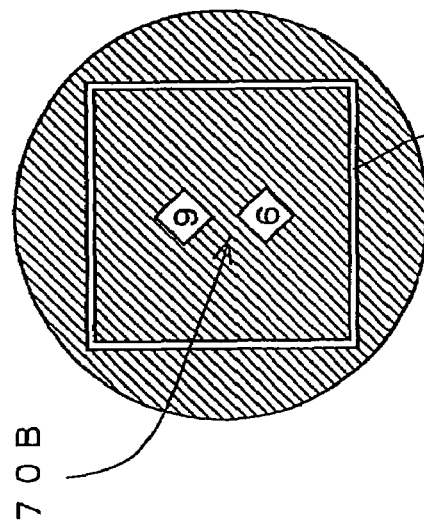
FIG.16(b) Right eye
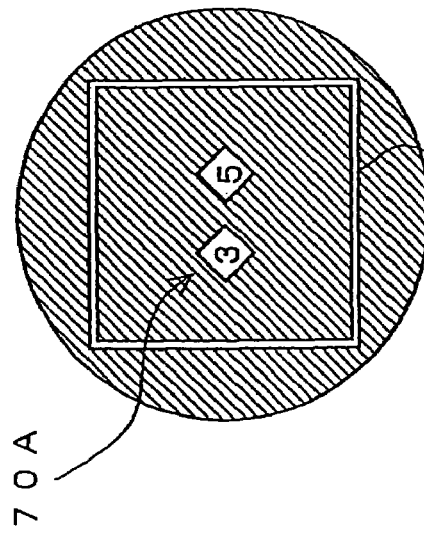
FIG.16(c) Both eyes

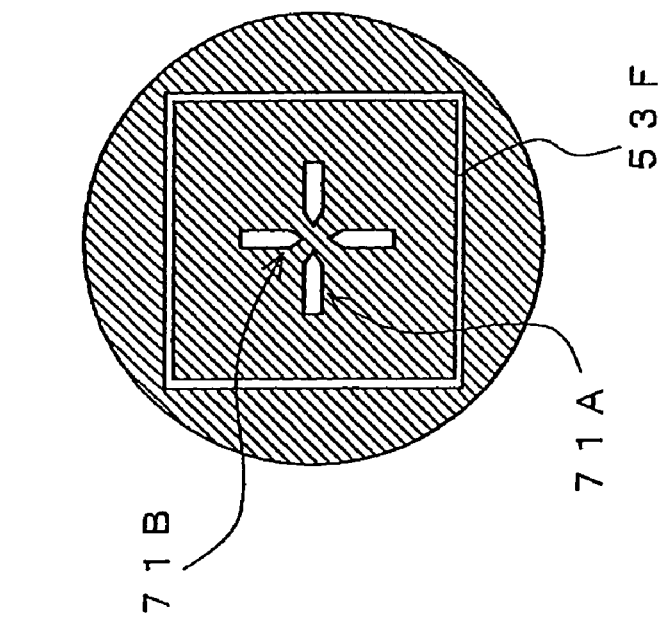
FIG.19(a) Left eye
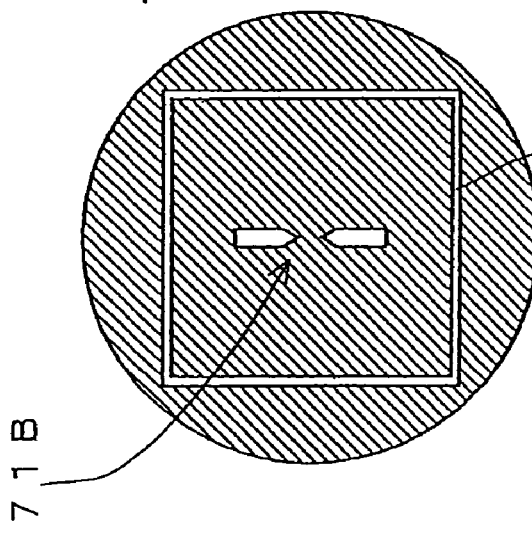
FIG.19(b) Right eye
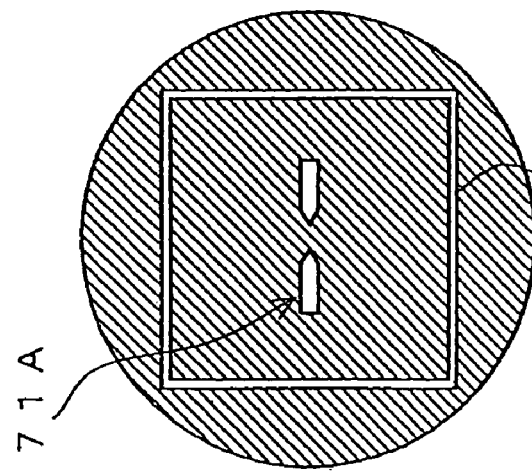
FIG.19(c) Both eyes

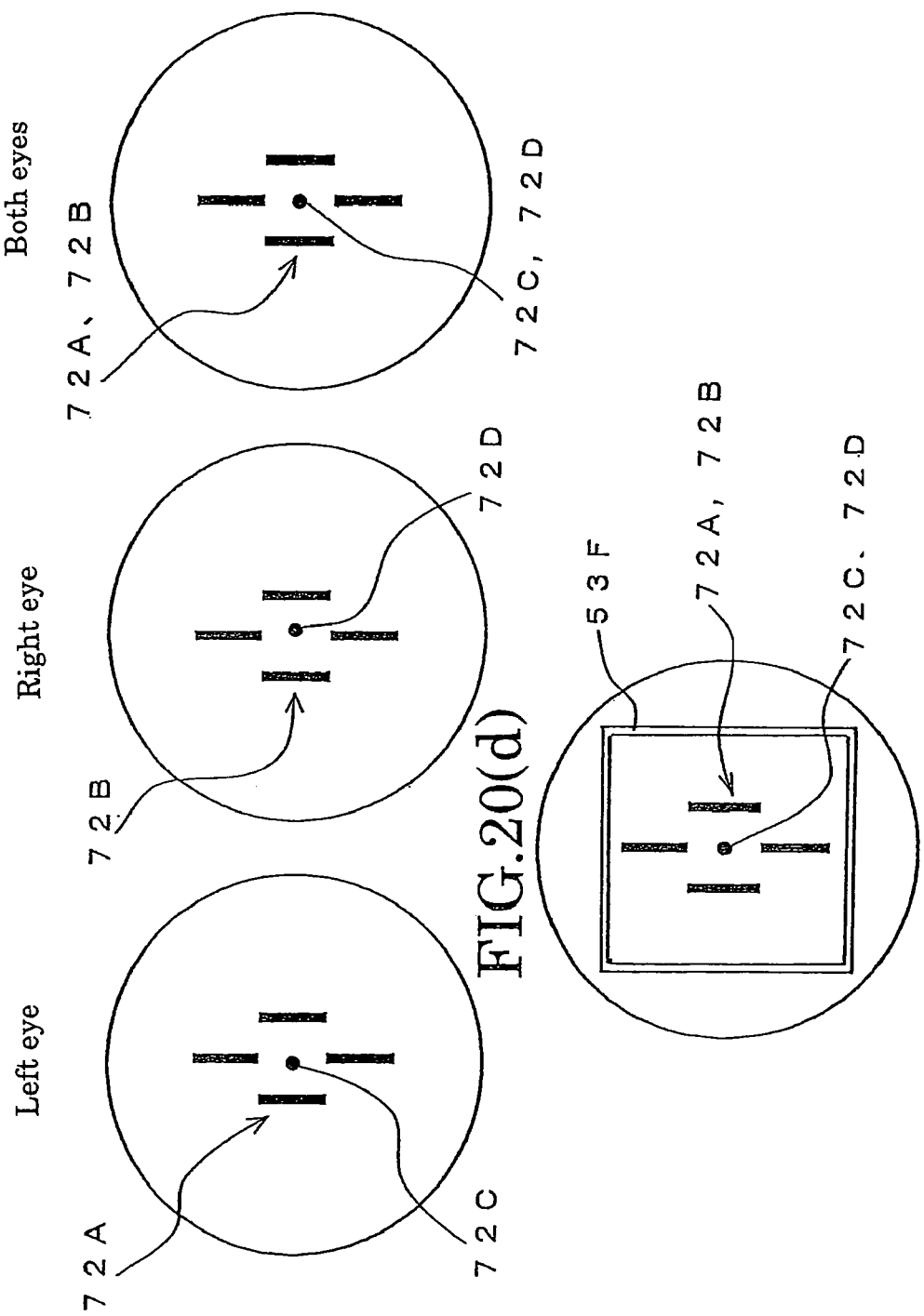

Landolt ring for visual acuity examination

FIG.29

Customer No.: | 10-digit serial number |   Name: [        ]   Age: [    ]

Date of examination: | July 26, 2000 |   PD: [    ]

|  | Spherical dioptric power | Astigmatic dioptric power | Cylinder axis |  | Visual acuity value |
|---|---|---|---|---|---|
| Dioptric power of spectacles: |  |  |  | Far visual acuity: |  |
| Right (R) |  |  |  | Right (R) |  |
| Left (L) |  |  |  | Left (L) |  |
|  |  |  |  | Both eyes |  |

Visual acuity value

Contact-lens corrected visual acuity: Right (R) [    ]
Left (L) [    ]

Visual acuity value

Naked-eye visual acuity: Right (R) [    ]
Left (L) [    ]
Both eyes [    ]

|  | Spherical dioptric power | Astigmatic dioptric power | Cylinder axis |  | Visual acuity value |
|---|---|---|---|---|---|
| Objective refractivity: |  |  |  | Far visual acuity: |  |
| Right (R) |  |  |  | Right (R) |  |
| Left (L) |  |  |  | Left (L) |  |
|  |  |  |  | Both eyes |  |

|  | Spherical dioptric power | Astigmatic dioptric power | Cylinder axis° |  | Visual acuity value |
|---|---|---|---|---|---|
| Recommended refractivity: |  |  |  | Far visual acuity: |  |
| Right (R) |  |  |  | Right (R) |  |
| Left (L) |  |  |  | Left (L) |  |
|  |  |  |  | Both eyes |  |

Addition power    Visual acuity value

Near addition power: Right (R) [    ]   Near visual acuity: [    ]
Left (L) [    ]   Both eyes Heterophoria test: "BO △" or "Right eye BU △" or "Requires close examination"
Stereoscopic test: "Normal" or "Requires close examination"
Comment: e.g.: "Difference of refractivity of both eyes is 2.0D."

OPTOMETRIC DEVICE

TECHNICAL FIELD

The present invention relates to an optometric apparatus which enables optometric measurement by an examinee himself/herself or an optometric assistant with less experience.

BACKGROUND ART

There is known an optometric apparatus constituted so that ocular refractivity of the right and left eyes of an examinee can be measured at the same time subjectively and objectively (See Japanese Patent Laid-Open No. 2000-83900).

This conventional optometric apparatus is so constituted that the examinee takes optometry following instructions of an optometrist.

However, optometric measurement of the examinee by the optometrist is not favorable in view of efficient management and cost reduction.

Also, recently, in the case of accommodative functional disorder such as near-vision disorder, asthenopia, sense of blear, etc. or in the case that abnormality of convergence and accommodation systems are suspected, when carrying out prescription of spectacles for reading or health management of VDT (video display terminal) workers and so on, accommodative functions such as accommodative near point, accommodative ability and accommodative dynamics are measured. For measurement of accommodative functions, subjective methods such as Ishihara's near point meter and accommodo-poly-recorder and objective methods such as infrared optometer and front-open type infrared optometer are used.

For measurement of subjective accommodative near point, 0.6 Landolt-ring targets and bar targets on near-distance optotypes are usually made to approach from the distance where an examinee can see the clearest at a constant rate of a target moving speed of 2.5 cm/sec to 5 cm/sec, and the distance where occurrence of even a slight blur is sensed is recorded as a near point.

The infrared optometer of the objective method has renovated a normal autorefractometer, in which an ocular refractive state of horizontal meridians when a target is moved at a constant speed is continuously measured so as to record dynamic characteristics of accommodation. The front-open type optometer records accommodation change of both eyes by moving a real space in front of the eyes with the target as an external target in the state close to natural vision.

However, in the subjective measurement of accommodative near point, after an examinee has learned blur of targets and subjective sensing standard of clear vision by practice, a distance where blur is sensed when a target is moved from a long distance to a short distance (disappearance threshold) and a distance where clear vision is enabled when the target is moved from the short distance to the long distance on the contrary (appearance threshold) are measured 3 times, respectively, and an average value of the both is set as a near point.

The measurement depends on subjective response and is subject to large fluctuation due to instability in subjective sensing standard between blur and clear visions of targets and uncertainty in target following motion and response of the examinee, which is particularly unsuitable for measurement of infants.

The measurement by the infrared optometer is carried out with one eye shielded and a target moved on the optical axis of one eye as accommodation stimulation, and it is different from daily relations between convergence and accommodation.

Accommodation and convergence are increased/decreased together in the daily life and in an unseparable relation with each other. Accommodation measurement with one eye shielded has a problem that accurate measurement of accommodative near point and accommodative ability is not possible.

With the measurement by the front-open type infrared optometer, external targets are utilized to present targets in the state closer to the natural vision, but it has a problem that a range of target movement is restricted and accommodative near point including far point can not be measured.

The present invention has been made in view of the above circumstances and its object is to provide an optometric apparatus which enables optometric measurement by an examinee himself/herself or an optometric assistant with less experience.

Also, an object of the present invention is to provide an optometric apparatus which presents targets to both eyes while maintaining the relation between accommodation and convergence, capable of measurement of accommodative functions in a wide target moving range, maintains the relation between accommodation stimulation and convergence constant, capable of easy measurement of accommodation regardless of refraction error of an examinee, and is suitable for diagnosis of cases such as near-vision disorder, asthenopia, blear, etc. and suspected abnormality in convergence and accommodation systems in the clinical ophthalmology as well as judgment when carrying out prescription of spectacles for reading and health management of VDT (video display terminal) workers, especially an optometric apparatus which can easily measure the relation between accommodation and convergence.

DISCLOSURE OF INVENTION

An optometric apparatus according to claim 1 is characterized in that optometric apparatus bodies which are driven independently in fore-and-aft, right-and-left and up-and-down directions, respectively, for respective optometry of an examinee are provided on both sides of a face receiving device.

The optometric apparatus according to claim 2 is characterized in that the optometric apparatus bodies have a function to measure objective refraction and subjective refraction of both eyes at the same time, and a mechanism rotating with a cycloduction point of the right and the left eyes to be examined as a center is provided.

The optometric apparatus according to claim 3 is characterized in that an auto-alignment mechanism for automatically executing alignment for eyes to be examined is provided on the optometric apparatus bodies.

The optometric apparatus according to claim 4 is characterized in that a monitor screen to present an image of an anterior ocular segment of eye to be examined to an optometric assistant is provided at each of the optometric apparatus bodies.

The optometric apparatus according to claim 5 is characterized in that a monitor screen for explanation of optometry procedure by the examinee himself/herself through movie playing is provided.

The optometric apparatus according to claim 6 is characterized in that comparison can be made between a vision when recommended spectacles are worn and a vision with naked eyes or with dioptric power of currently used glasses.

The optometric apparatus according to claim 7 is characterized in that the optometric apparatus is connected to a lens meter for measuring optical characteristics of a pair of spectacle lenses mounted to a spectacle frame, data of the optical characteristics of the spectacle lenses is inputted from the lens meter, and an initial value of PD value at auto-alignment is set based on the PD value as the optical characteristics data.

The optometric apparatus according to claim 8 is characterized in that the lens meter measures the optical characteristics of the pair of spectacle lenses mounted to the spectacle frame at the same time.

The optometric apparatus according to claim 9 is characterized in that the auto-alignment is carried out while maintaining the PD value.

The optometric apparatus according to claim 10 is characterized in that an initial value of PD value is set according to age and sex of the examinee.

The optometric apparatus according to claim 11 is characterized in that an initial setting of PD value is cancelled when alignment for one of the right and left eyes to be examined is gained, and data of the alignment is used as the alignment data for the other eye to be examined so that alignment of the other eye to be examined can be automatically executed.

The optometric apparatus according to claim 12 is characterized in that an image of an anterior ocular segment of the eye to be examined is presented on the monitor screen for explaining the optometry procedure by the examinee himself/herself by the movie playing.

An optometric apparatus according to claim 13 is characterized in that an optometric apparatus body in which an optical system for presenting targets for a left eye to the left eye is built and an optometric apparatus body in which an optical system for presenting targets for a right eye to the right eye is built are provided.

The optometric apparatus according to claim 14 is characterized in that a fusion target presenting optical system for presenting fusion targets at binocular optometry of eyes to be examined is provided in each of the optical systems.

An optometric apparatus according to claim 15 is characterized in that an optometric apparatus body having a mirror opposing a left eye in which a measurement optical system for objective measurement of the left eye is built, an optometric apparatus body having a mirror opposing a right eye in which a measurement optical system for objective measurement of the right eye is built, and an optotypes examining device presenting optotypes from behind through the right and the left mirrors are provided.

The optometric apparatus according to claim 16 is characterized in that, after subjective refractive measurement for far targets, the targets are moved to a predetermined near distance and the right and the left optometric apparatus bodies are rotated with the cycloduction point of the right and the left eyes to be examined as the center according to the predetermined near distance so as to execute objective measurement of both eyes.

The optometric apparatus according to claim 17 is characterized in that there are provided a calculating means for calculating a difference between an objective refractive measurement value for the far targets and an objective refractive measurement value for the both eyes at the predetermined near distance and a determining means for determining accommodative functional disorder or necessity for the predetermined near distance based on the calculation result.

The optometric apparatus according to claim 18 is characterized in that, when moving the targets to the predetermined near distance, step feeding of the targets is executed so as to carry out the objective measurement for both eyes at the same time in every time of the execution of the step feeding.

The optometric apparatus according to claim 19 is characterized in that the targets are Landolt rings and by having a lever tilted in a direction of a cut in the Landolt ring to see if a direction in which the lever is tilted matches the direction of the cut, whether the examinee is paying attention to the Landolt ring or not is checked.

The optometric apparatus according to claim 18 is characterized in that, when the direction in which the lever is tilted matches the direction of the cut in the Landolt ring, objective measurement is started.

The optometric apparatus according to claim 19 is characterized in that different Landolt rings are presented to the examinee at every measurement if an average is to be obtained by executing the objective measurement several times.

BRIEF DESCRIPTION OF DRAWINGS

FIG. 16 is a view showing an example of a red and green chart, in which (a) shows the red and green chart for the left eye, (b) shows the red and green chart for the right eye and (c) shows how a target is seen when the right and the left red and green charts are seen with both eyes with emmetropia.

FIG. 19 is a view showing an example of cross heterophoria chart, in which (a) shows the cross heterophoria chart for the left eye, (b) shows the cross heterophoria chart for the right eye and (c) shows how a target is seen when both cross heterophoria charts are seen with emmetropic both eyes.

FIG. 20 is a view showing an example of a stereoscopic vision chart, in which (a) shows the stereoscopic vision chart for the left eye, (b) shows the stereoscopic vision chart for the right eye, (c) shows how a target is seen when the stereoscopic vision chart is seen by emmetropic both eyes and (d) shows the state where a fusion frame is presented.

FIG. 29 is a view showing an example of display of a measurement result.

BEST MODE FOR CARRYING OUT OF THE INVENTION

Figure 1:
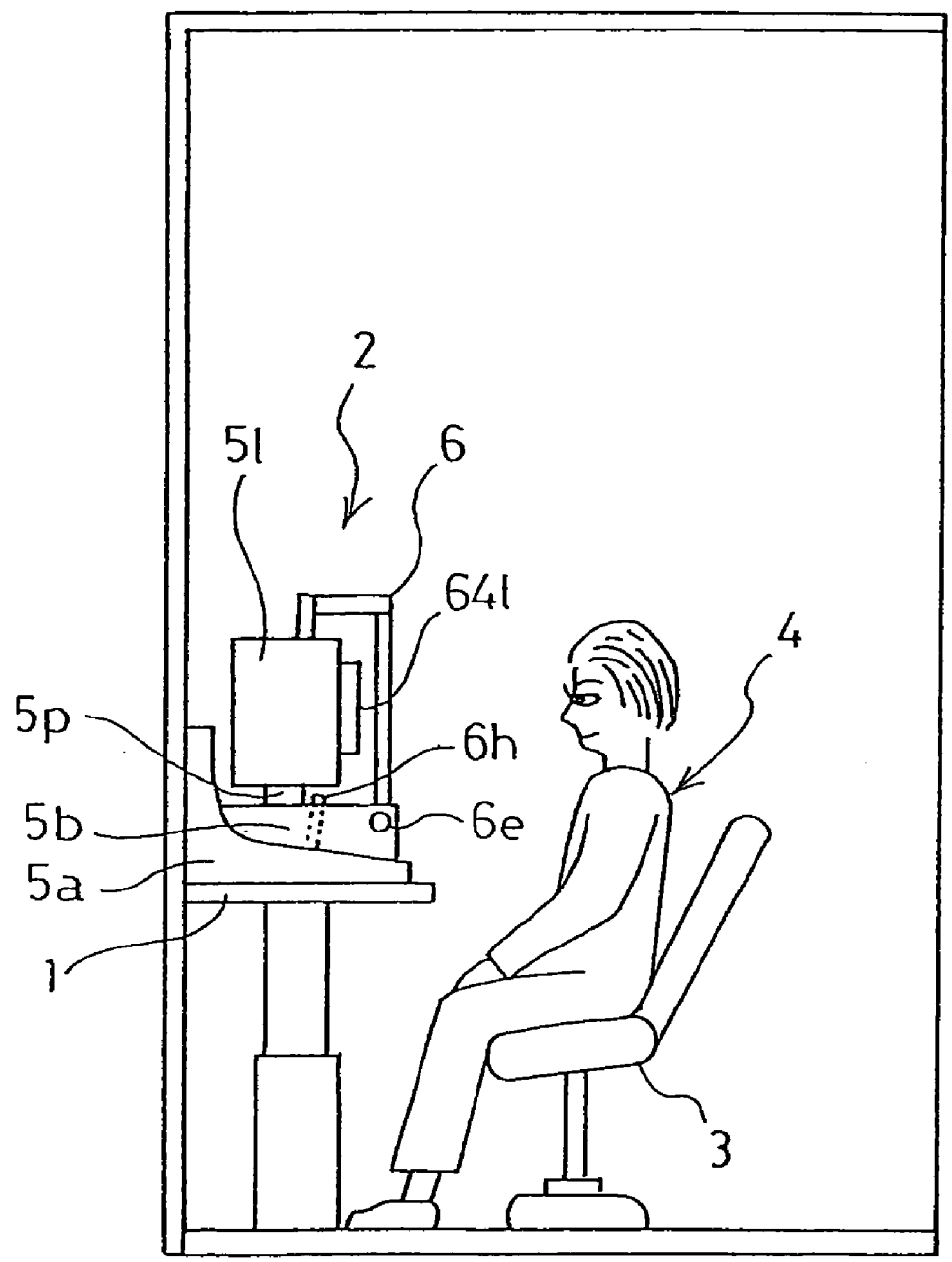
FIG. 1 is an explanatory view showing an outline of an optometric apparatus according to the present invention.
Figure 2:
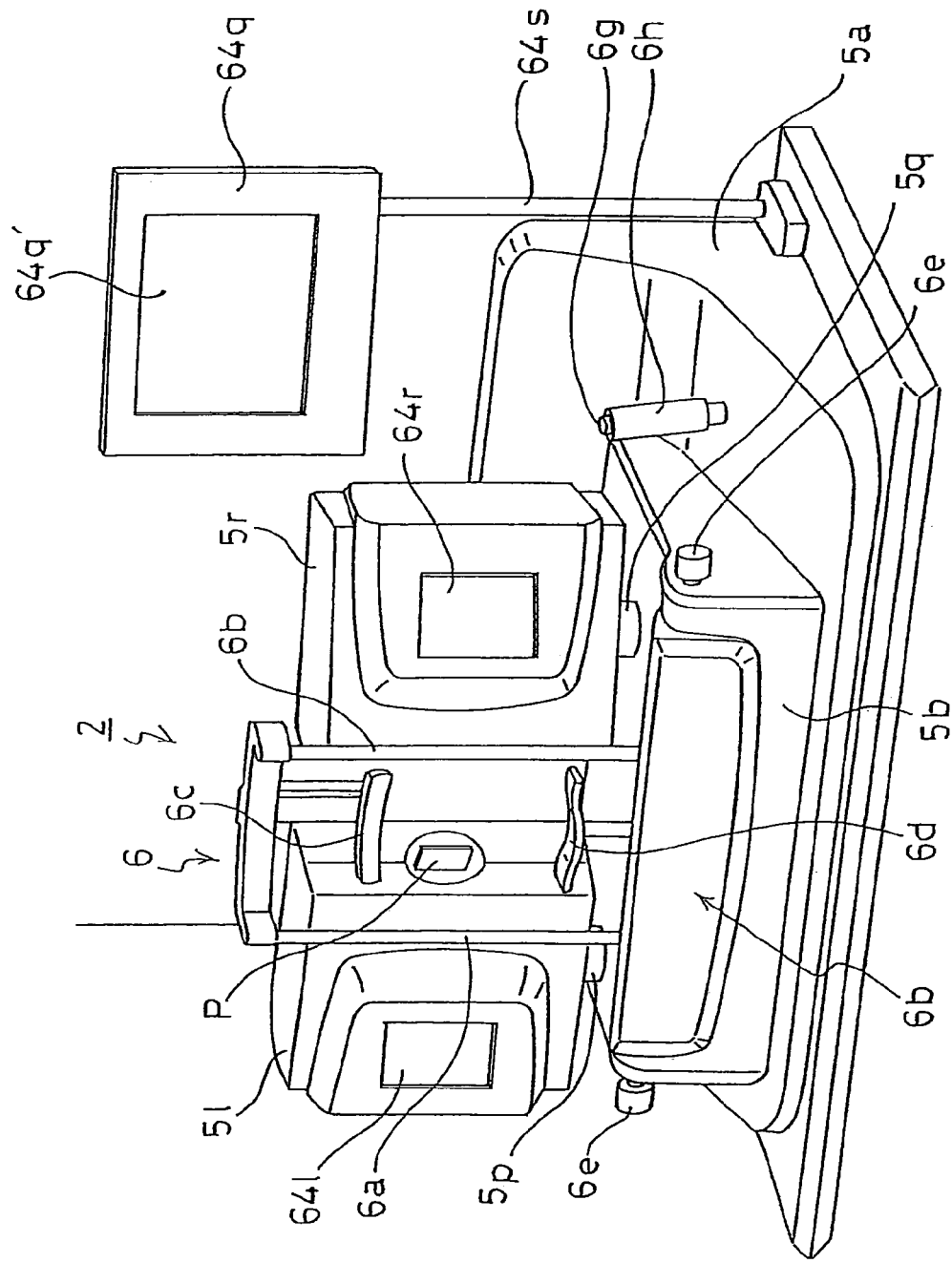
FIG. 2 is an appearance drawing of the optometric apparatus shown in FIG. 1.

In FIG. 1, 1 is an optometric table whose height can be adjusted vertically, 2 is an optometric apparatus disposed on the optometric table 1, 3 is an optometric chair and 4 is an examinee seated on the optometric apparatus. The optometric apparatus 2 has, as shown in FIG. 2, a base portion 5a, a driving mechanism box 5b, a right-and-left pair of body portions 5l and 5r with a built-in measurement optical system which will be mentioned later and a face receiving device 6. The body portions 5l and 5r are supported by supports 5p and 5q.

The face receiving device 6 is provided with a pair of supports 6a and 6b and a jaw receiver 6d. The pair of supports 6a and 6b is provided with an arc-state forehead receiver 6c. The jaw receiver 6d can be adjusted in the vertical direction by knobs 6e and 6e. Also, the forehead receiver 6c can be adjusted in the fore-and-aft direction.

In the driving mechanism box 5b, an XYZ driving mechanism (not shown) for independently driving the supports 5p and 5q, respectively, are provided. For this XYZ driving mechanism, a pulse driving motor and a feeding screw are used, for example, and a known constitution can be employed. Also, in the driving mechanism box 5b, a rotary driving mechanism for rotating and driving the supports 5p and 5q independently in the horizontal and opposite direction to each other is provided. In this rotary driving mechanism, combination of a pulse motor and a gear may be used. The body portions 5l and 5r have a function for objective measurement and subjective refractive measurement for both eyes at the same time and are rotated with the cycloduction point of the right and left eyes to be examined as the center.

A joystick lever (hereinafter referred to as a lever) 6h is provided on the base 5a, and this lever 6h is provided with a button 6g.

Figure 3:
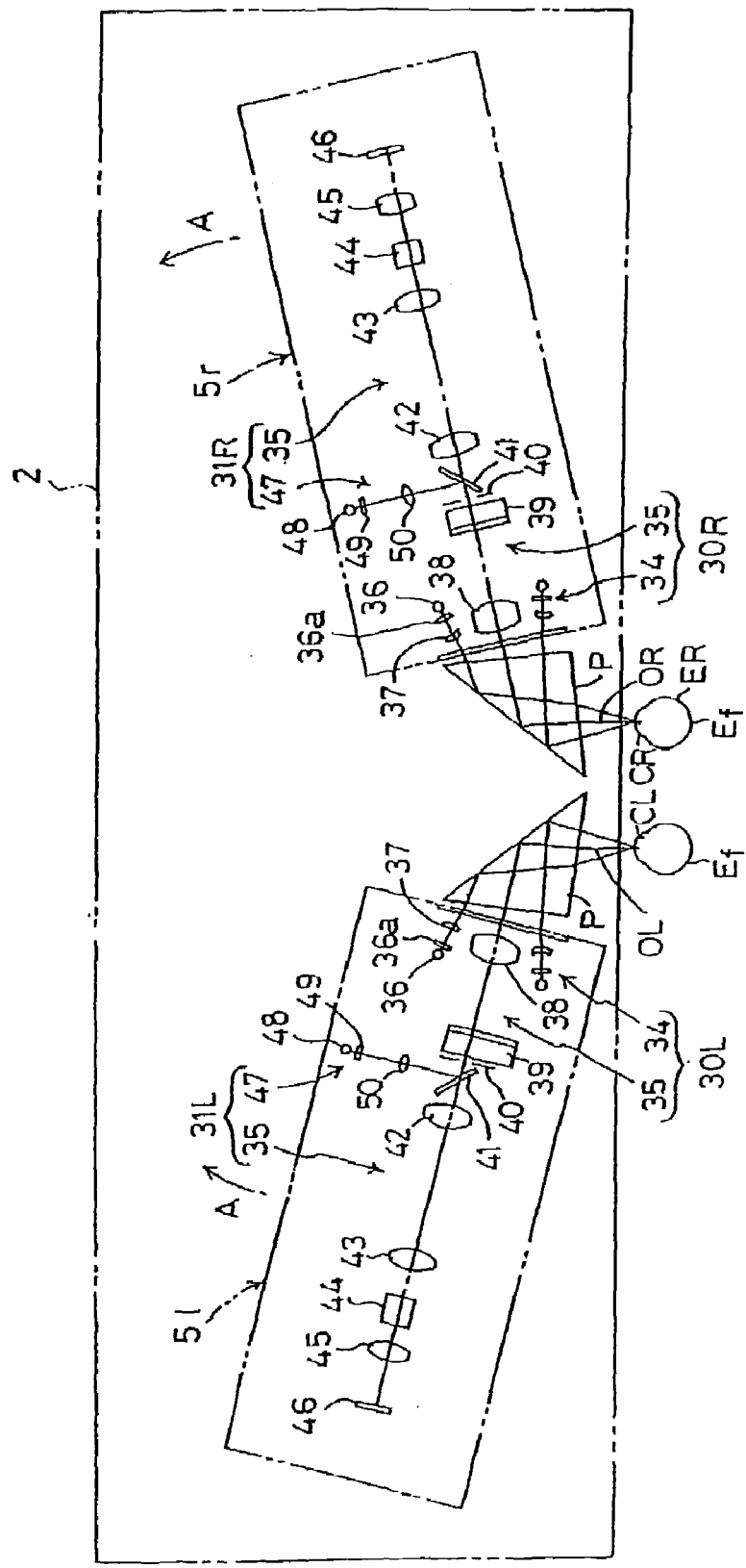
FIG. 3 is a view showing an optical system of the optometric apparatus shown in FIG. 1.
Figure 4:
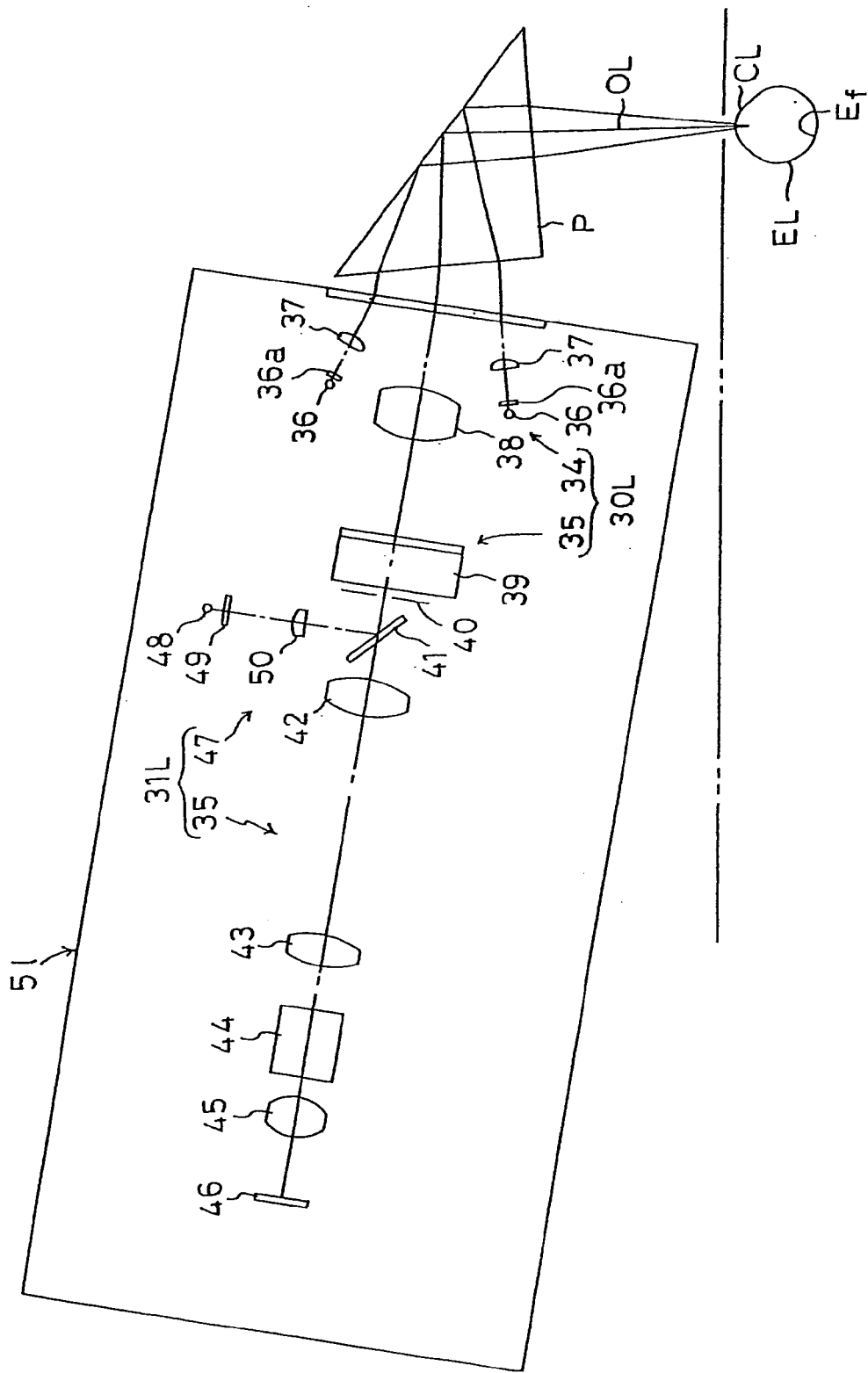
FIG. 4 is a view showing the optical system for the left eye shown in FIG. 3 in the enlarged manner.
Figure 5:
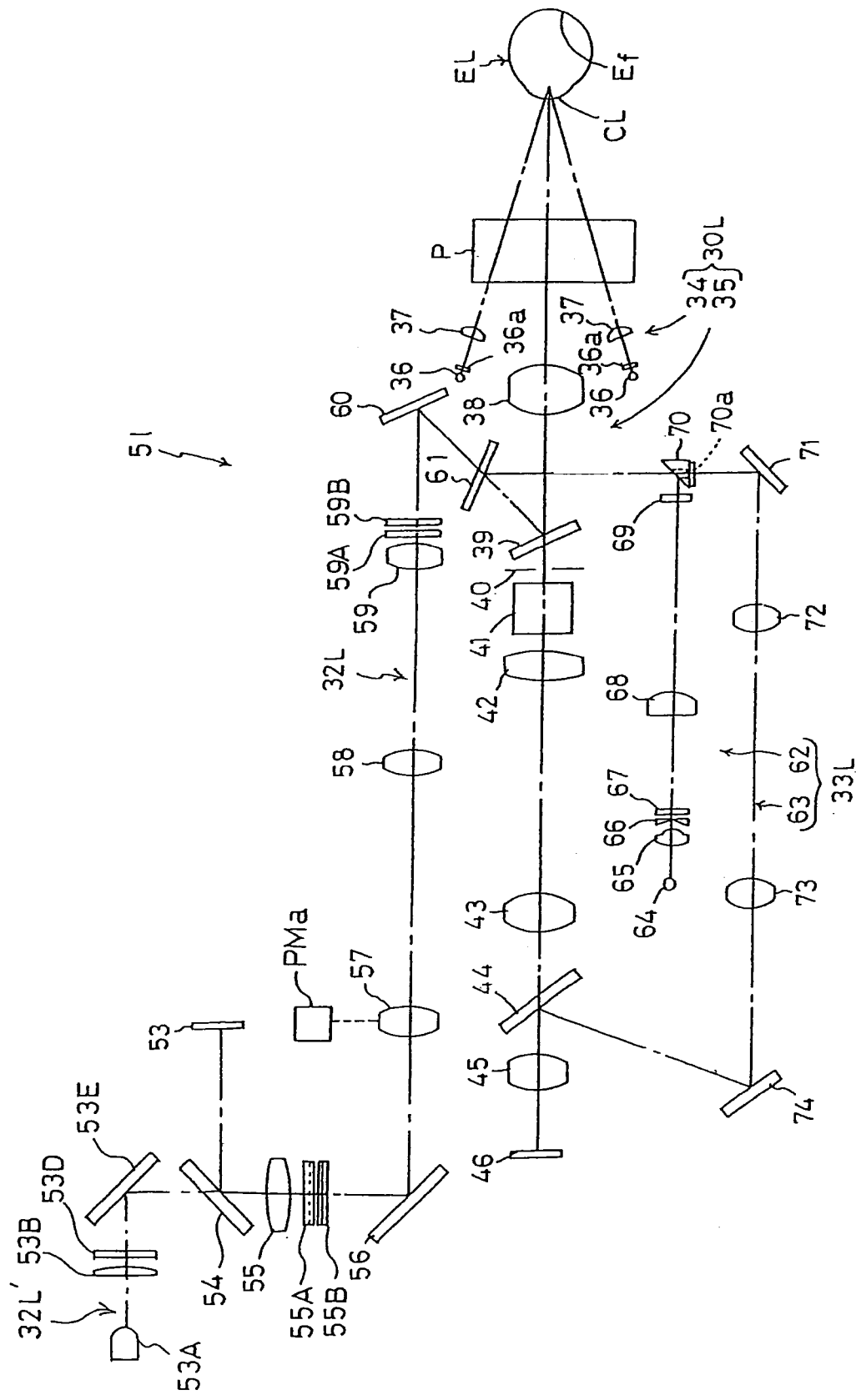
FIG. 5 is a plan view of the optical system for the left eye shown in FIG. 4.
Figure 6:
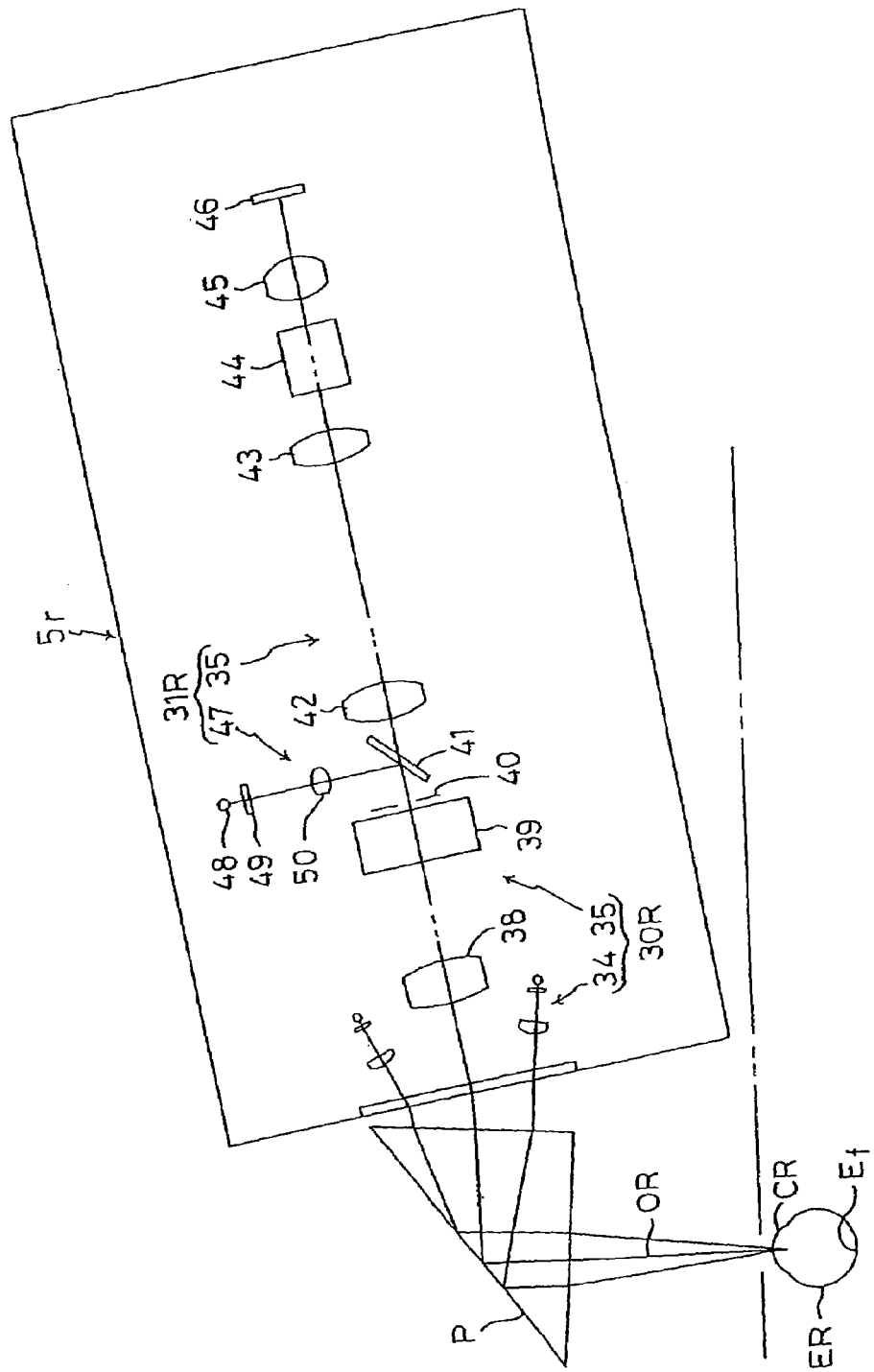
FIG. 6 is a view showing the optical system for the right eye shown in FIG. 3 in the enlarged manner.

The measurement optical system of the body portion 5l has an anterior ocular segment photography optical system 30L shown in FIGS. 3 through 5, an XY alignment optical system 31L, a fixation optical system 32L and a refractive measurement optical system 33L. The measurement optical system of the body portion 5r has an anterior ocular segment photography optical system 30R shown in FIGS. 3, 6 and 7, an XY alignment optical system 31R, a fixation optical system 32R and a refractive measurement optical system 33R. Since the measurement optical system of the body portion 5l and the measurement optical system of the body portion 5r are symmetrical, the measurement optical system of the body portion 5l will be explained.

The anterior ocular segment photography optical system 30L has an anterior ocular segment illumination optical system 34 and a photographic optical system 35. The anterior ocular segment illumination optical system 34 has a light source 36 for anterior ocular segment illumination, a diaphragm 36a and a projection lens 37 for projecting the light from the light source 36 to the anterior ocular segment of an eye E to be examined.

The photographic optical system 35 has a prism P into which a reflected light from the anterior ocular segment of the eye E to be examined enters, an objective lens 38, a dichroic mirror 39, a diaphragm 40, a dichroic mirror 41, relay lenses 42 and 43, a dichroic mirror 44, a CCD lens (imaging lens) 45, and a CCD (image pickup means) 46.

The XY alignment optical system 31L has an alignment illumination optical system 47 and a photographic optical system 35 as an alignment light-receiving optical system. The alignment illumination optical system 47 has, as shown in FIG. 4, an illumination light source 48 for alignment, a diaphragm 49 as an alignment target, a relay lens 50, the dichroic mirror 41, the diaphragm 40, the dichroic mirror 39, the objective lens 38 and the prism P.

The fixation optical system 32L has a liquid crystal display 53 for displaying fixation targets and charts for subjective optometry, a half mirror 54, a collimator lens 55, rotary prisms 55A and 55B, a reflecting mirror 56, a moving lens 57, relay lenses 58 and 59, cross cylinder lenses (VCC lenses) 59A and 59B, a reflecting mirror 60, dichroic mirrors 61 and 39, the objective lens 38 and the prism (may be a mirror) P.

Figure 23:
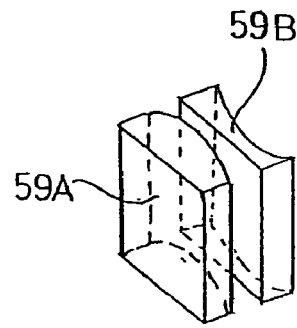
FIG. 23 is a perspective view showing an example of a cross cylinder lens.
Figure 30:
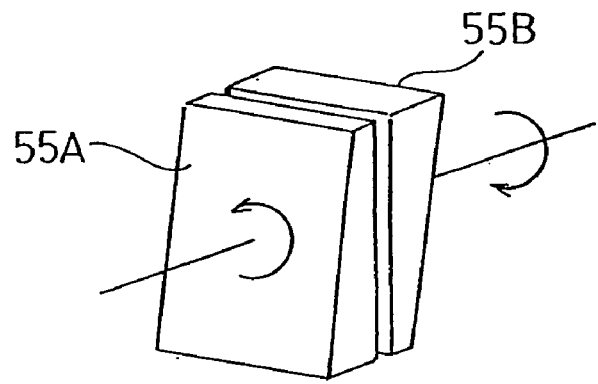
FIG. 30 is a perspective view showing an example of a rotary prism.

For the rotary prisms 55A and 55B, publicly known ones shown in FIG. 30 are used, and when they are rotated in the direction opposite to each other, a prism amount can be continuously changed, while when rotated integrally in the same direction, a prism base direction is rotated. The rotary prisms 55A and 55B presents a target 71A shown in FIG. 19(a) to the left eye and a target 71B shown in FIG. 19(b) to the right eye to be used for heterophoria measurement. For emmetropia, as shown in FIG. 19(c), the target 71A and the target 71B are crossed with each other at the center, but if there is heterophoria, they are separated. The rotary prisms 55A and 55B are used, as shown in FIG. 19(c), for measurement of a prism amount with which the target 71A and the target 71B cross each other at the center. For the cross cylinder lenses (VCC lenses) 59A and 59B, those known shown in FIG. 23 are used, and when they are rotated in the direction opposite to each other, astigmatic dioptric power is changed, while when they are rotated integrally in the same direction, the cylinder axis is rotated.

Here, the targets are presented using the liquid crystal display 53, but those known which presents targets by background illumination can be used by providing targets on a turret disk.

In the fixation optical system 32L, the moving lens 57 can be moved in the optical axis direction by a pulse motor PMa according to refractive power of an eye to be examined. By this, fixation and fogging for the eye to be examined is enabled.

Figure 24:
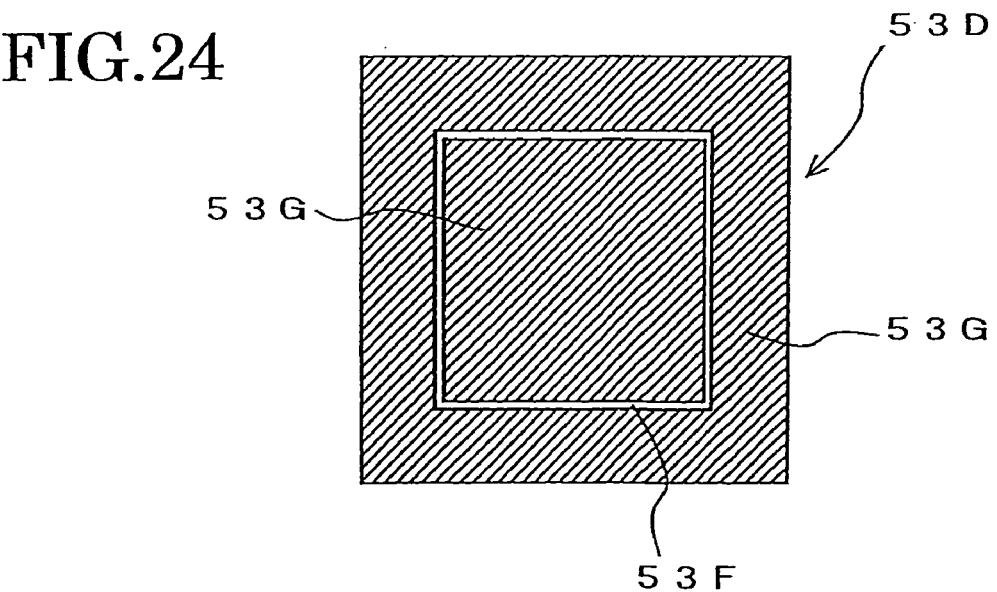
FIG. 24 is a view showing an example of a fusion frame chart.

At the fixation target optical system 32L, a fusion target presenting optical system 32L' is provided. The fusion target presenting optical system 32L' is constituted by an LED 53A as an illumination light source, a collimator lens 53B, a fusion frame chart 53D and a total reflection mirror 53E. At the fusion frame chart 53D, as shown in FIG. 24, a square-shaped transmission window 53F and a light-shielding portion 53G are formed. On the collimator lens 53B, a diffusion surface is provided so that the fusion frame chart 53D is evenly illuminated.

In the embodiment of the present invention, the fusion target presenting optical system 32L' is provided, but a fusion frame 53F can be directly provided at a target of the liquid crystal display 53.

The refractive measurement optical system 33L has a measurement flux projecting optical system 62 and a measurement flux light-receiving optical system 63. The measurement flux projecting optical system 62 has a light source 64 for measurement such as an infrared LED, a collimator lens 65, a conical prism 66, a ring target 67, a relay lens 68, a ring-state diaphragm 69, a perforated prism 70 with a through hole 70a formed at the center, the dichroic mirrors 61 and 39, the objective lens 38 and the prism P.

Also, the measurement flux light-receiving optical system 63 has the prism P for receiving reflected light from an fundus oculi Ef of the eye E to be examined, the objective lens 38, the dichroic mirrors 39 and 61, the through hole 70a of the perforated prism 70, a reflecting mirror 71, a relay lens 72, a moving lens 73, a reflecting mirror 74, the dichroic mirror 44, the CCD lens 45 and CCD 46. Since the optical system of the body portion 5r is almost the same as the optical system of the body portion 51, its explanation is omitted.

Figure 8:
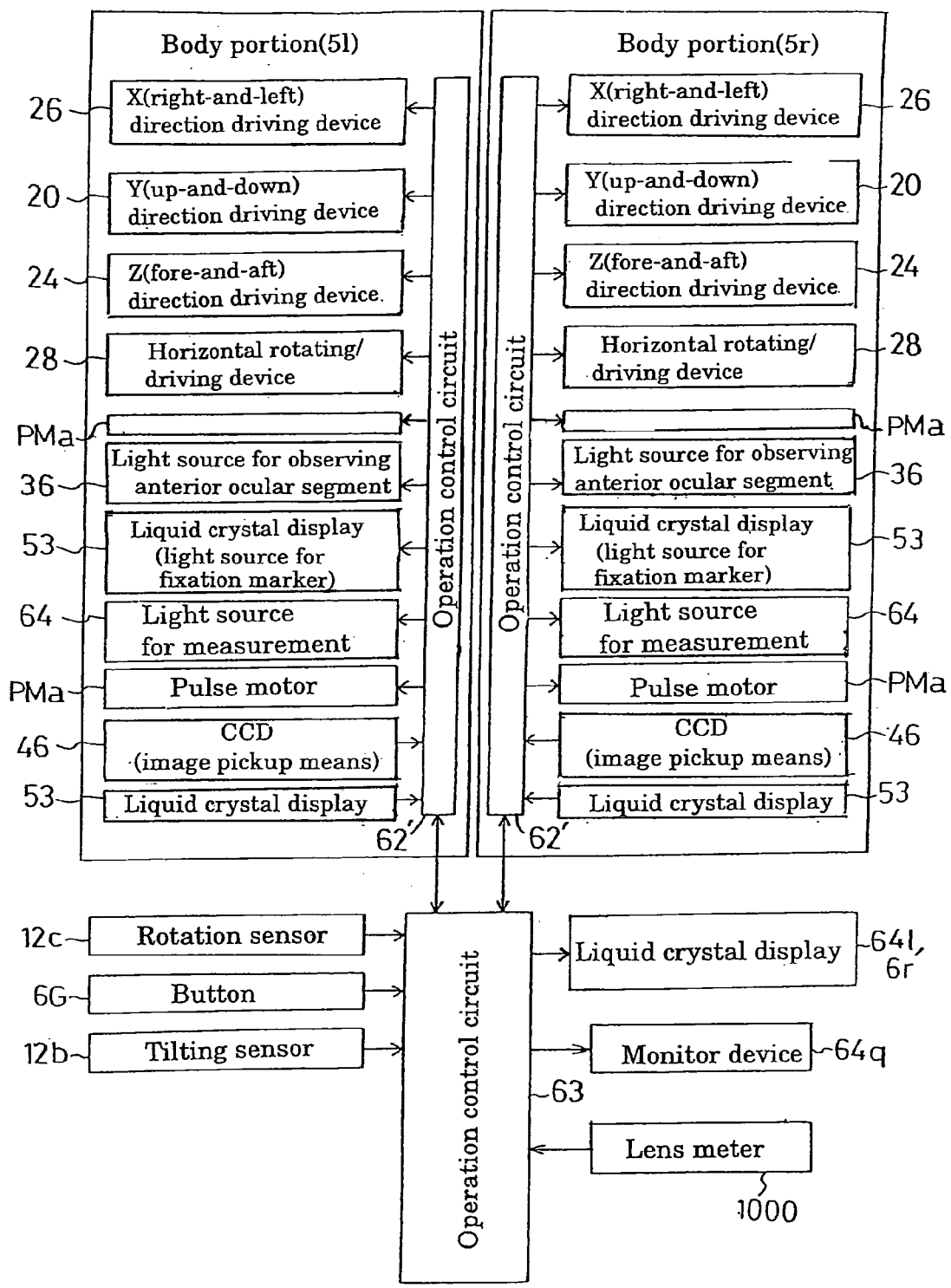
FIG. 8 is a block diagram of a control system of the optometric apparatus according to the present invention.

The control system of the body portions 5l and 5r is shown in FIG. 8. The driving devices 20, 24, 26, and 28, the illumination light source 36 for observing the anterior ocular segment, the liquid crystal display (fixation target light source) 53, the light source 64 for measurement, the pulse motor PMa, etc. are operated/controlled by an operation control circuit 62 shown in FIG. 8. Also, into the operation control circuit 62, a detection signal from the CCD 46 is inputted. The control system of the body portion 5r is the same as the control system of the body portion 5l.

The entire control circuit has, as shown in FIG. 8, an operation control circuit 63 for controlling control circuits 62' and 62' of the body portions 5l and 5r. To this operation control circuit 63, a tilting detection sensor 12b for detecting tilting operation of the button 6g and the lever 6h and a rotation sensor 12c for detecting rotating operation around the axis of the lever 12 are connected. Also, to the operation control circuit 63, liquid crystal displays 64l and 64r as monitor devices and a monitor device 64q are connected. The liquid crystal display 64l is, as shown in FIG. 2, provided on the front of the body portion 5l to play a role of displaying an anterior ocular segment image of the left eye of the eye E to be examined. The display 64r is provided on the front of the body portion 5r to play a role of displaying an anterior ocular segment image of the right eye of the eye E to be examined. The monitor device 64q is mounted to a support 64s set up on the base 5a. The monitor device 64 presents a monitor screen for explaining measurement procedures by an examinee himself/herself on its display screen 64q' by movie playing.

Figure 9A:
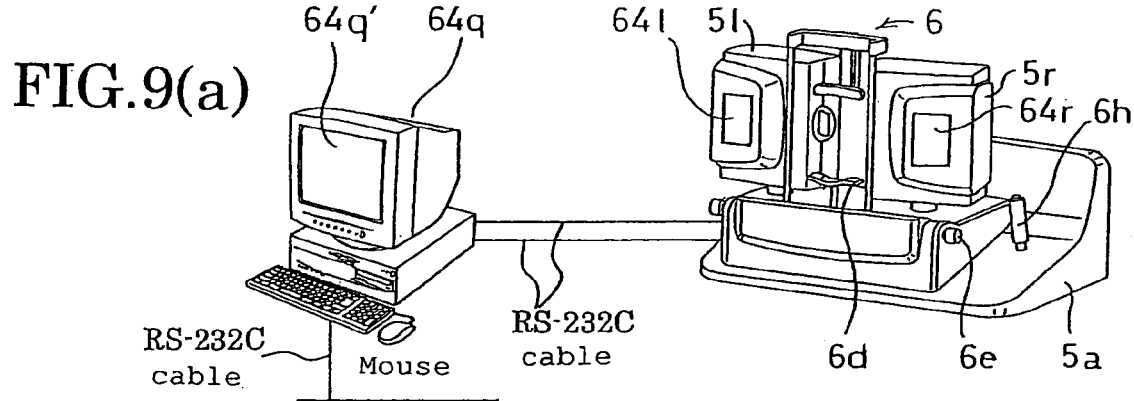
FIG. 9 is a view showing a connection form between the optometric apparatus and a lens meter, in which (a) is an explanatory view showing the state where the lens meter is disposed in the neighborhood of the optometric apparatus and connected to a monitor device through an RS232C cable, (b) is a view showing the state where the lens meter is disposed far from the optometric apparatus and the lens meter and the optometric apparatus are connected to the monitor device through the RS232C cable, and (c) is a view showing the state where a plurality of the optometric apparatuses and the monitor devices are arranged and the lens meter is connected to the monitor device through LAN.
Figure 9B:
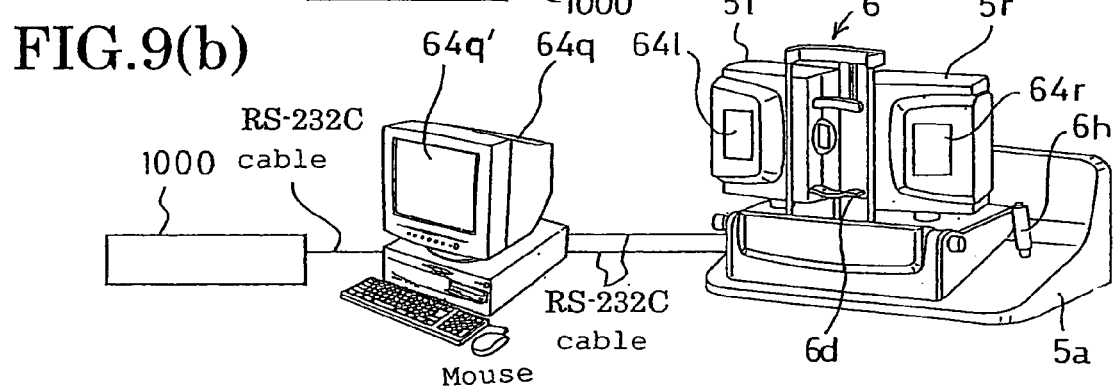
Figure 9C:
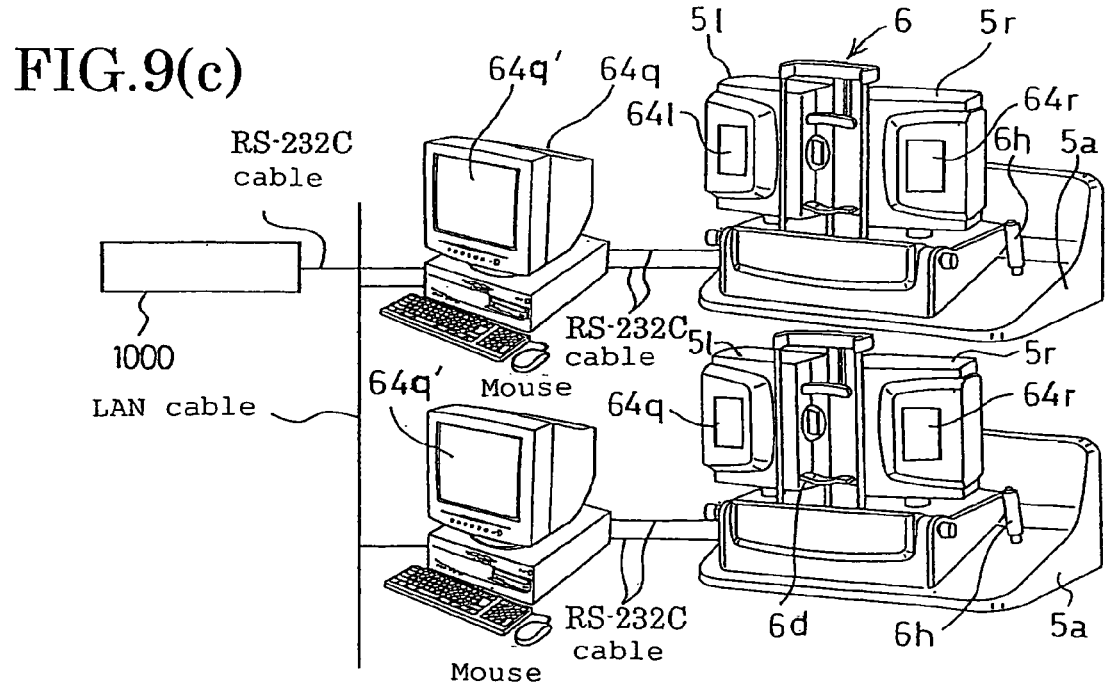
Figure 10:
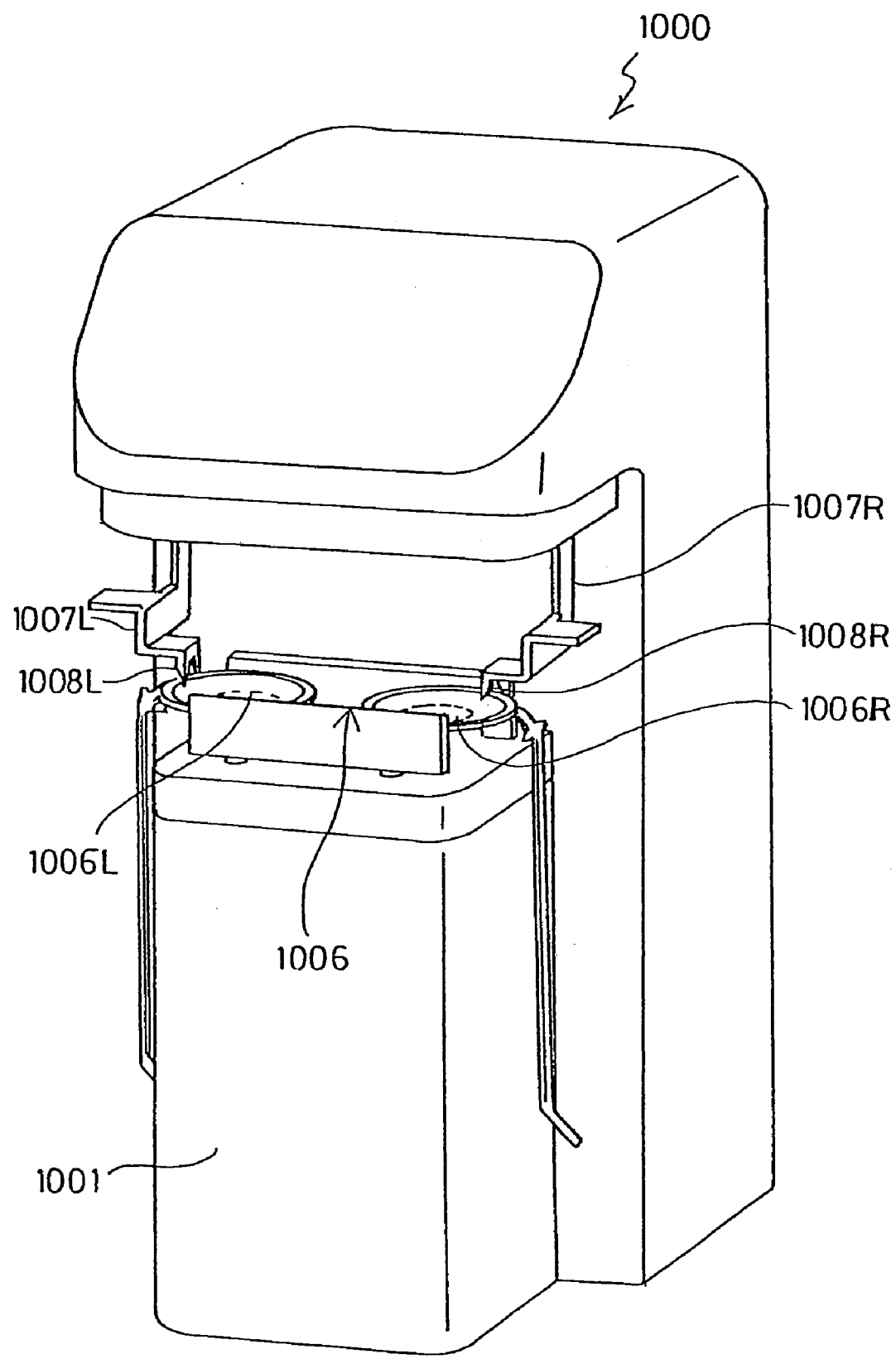
FIG. 10 is an appearance view of the lens meter shown in FIG. 9.

To the optometric apparatus, a lens meter 1000 is connected. The connection form of the lens meter 1000 can be any of FIGS. 9(a) to 9(c). The appearance of the lens meter 1000 is shown, for example, in FIG. 10. This lens meter 1000 has a function to measure optical characteristics of spectacle lenses 1006L and 1006R with right and left frames of spectacles 1006 at the same time. In FIG. 10, 1007L and 1007R are push levers of the spectacle lenses 1006L and 1006R. When the spectacles 1006 are placed on a spectacle set table 1001 of this lens meter 1000, a detection pin (not shown) provided on the spectacle set table 1001 detects setting of the spectacles 1006. By this, the push levers 1007L and 1007R are automatically lowered, the spectacles 1006 are fixed by pressing claws 1008L and 1008R, and the optical characteristics data of the right and left spectacle lenses 1006L and 1006R is taken at the same time by the measurement optical system built in the lens meter 1000. Also, based on the optical characteristics data of the right and left spectacle lenses 1006L and 1006R, a PD value of the examinee (who wears glasses) is obtained. For the structure of the measurement optical system of this lens meter 1000, two publicly known measurement optical systems can be used in principle, and detailed constitution is described, for example, in the Japanese Patent Application No. 2000-399801. In the embodiment of the present invention, the lens meter shown in FIG. 10 is used, but publicly known autolens meter having a PD measurement function can be also used.

Figure 11A:
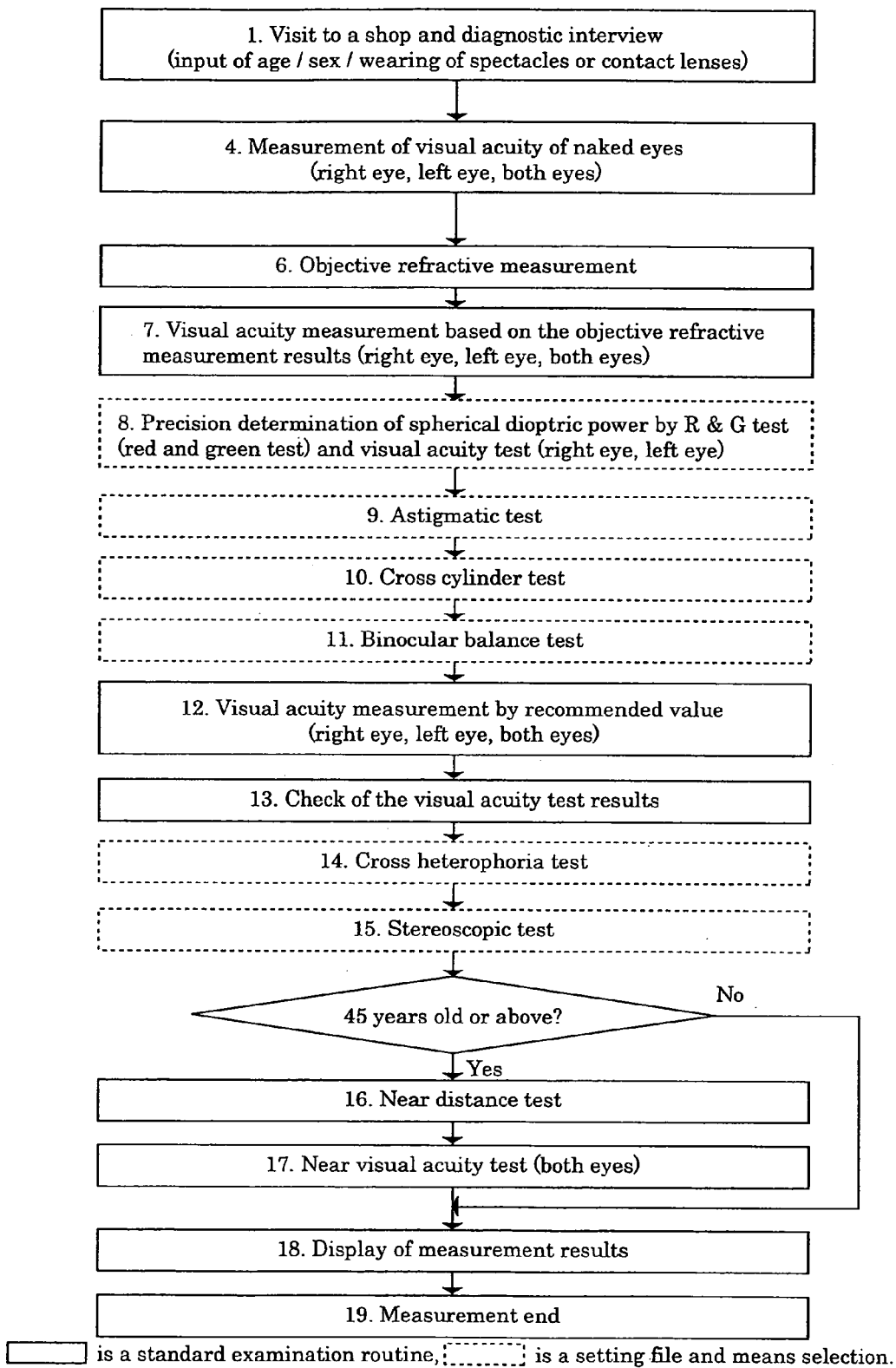
FIG. 11 is a flowchart showing an example of optometric procedures of the optometric apparatus according to the present invention, in which (a) is a flowchart for those who have not worn spectacle glasses or contact lenses, (b) is a flowchart for those who wear spectacle glasses, and (c) is a flowchart for those who wear contact lenses.
Figure 11B:
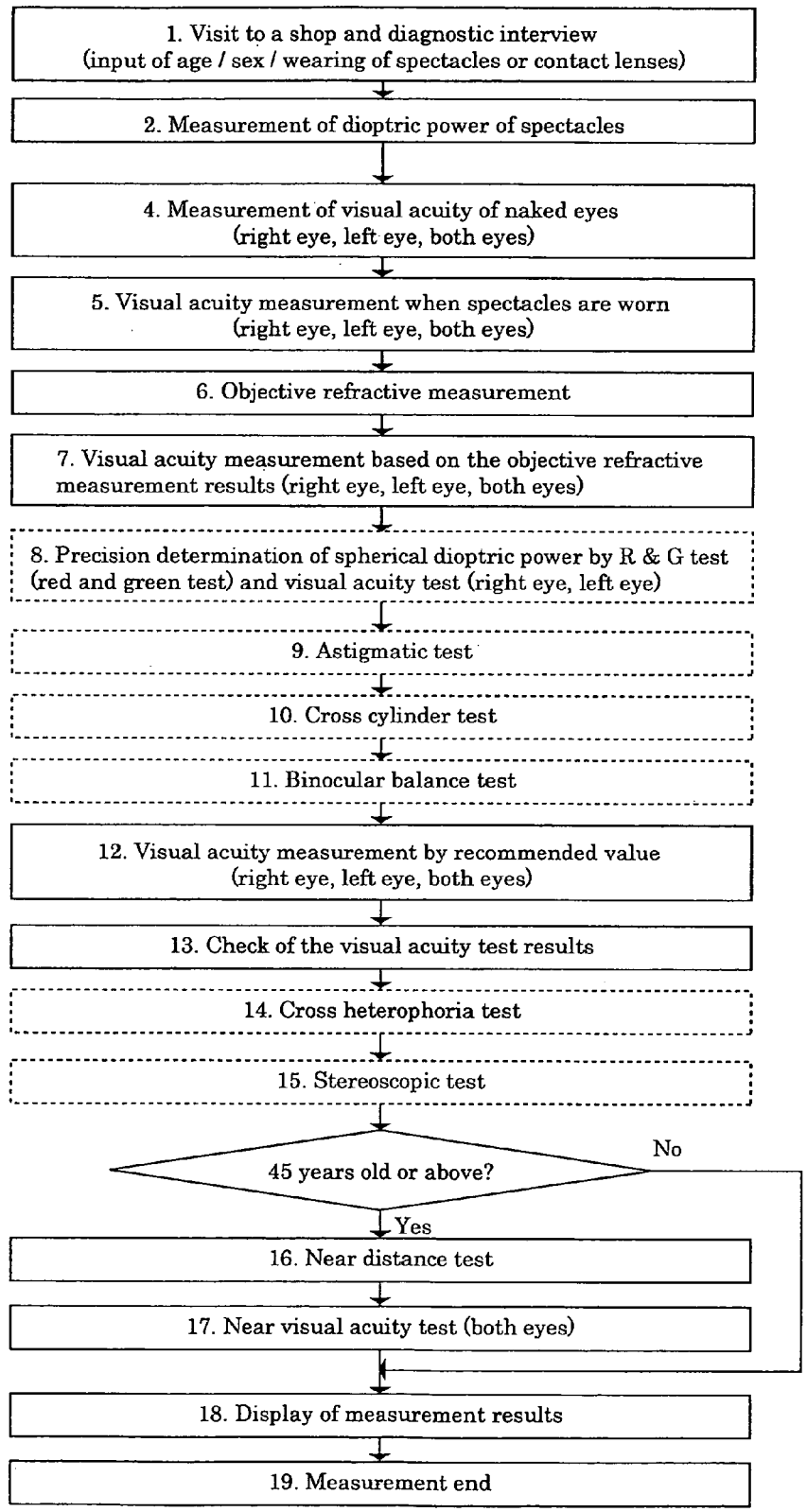
Figure 11C:
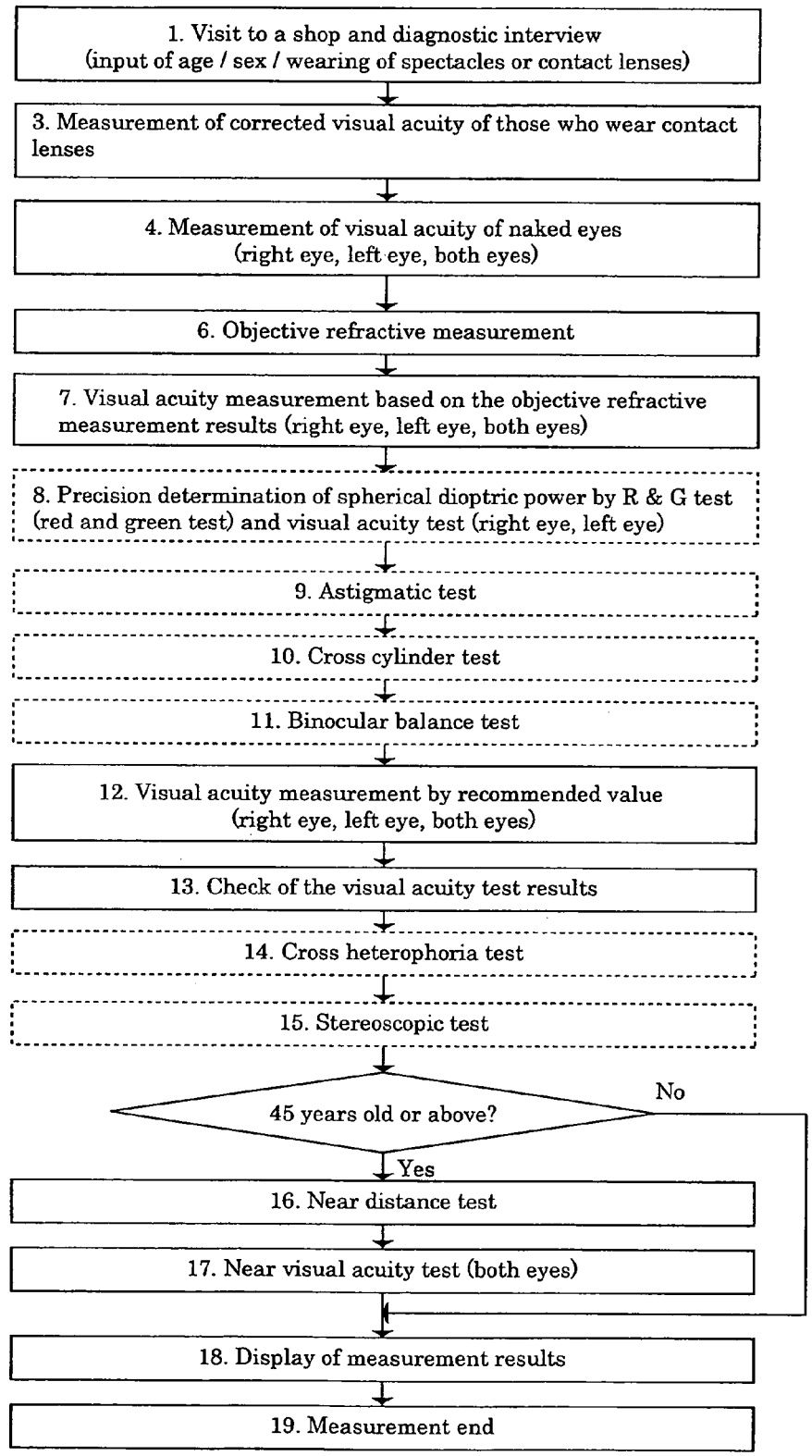

The optical characteristics data of the spectacle lenses of the lens meter 1000 is inputted into the operation control circuit 63. The operation control circuit 63 also plays a role to display an optical characteristics value of the spectacle lenses, a PD value, on a display screen 64q' of the monitor device 64q. It is preferable to make initial setting of the body portions 5l and 5r using this PD value in the case of wearers of spectacle lenses. In this optometric apparatus 2, an optometry routine shown in FIGS. 11(a) through (c) can be executed respectively for those who have not worn spectacles or contact lenses, for examinees who wear spectacles and for examinees who wear contact lenses. The details of this optometry routine will be described later.

Upon entry to a shop by an examinee, the monitor device 64q is turned on, and a predetermined matter is displayed on the display screen 64q'. According to the instructions displayed on the display screen 64q' of the monitor device 64q, the examinee operates a touch panel of the display screen 64q'. For example, the examinee inputs sex, age, wearing of spectacles/contact lens or not, etc. are inputted according to the instructions on the touch panel. At the same time, instruction matters are guided in voice.

For those who wear spectacles, the optical characteristics value data (dioptric power) of the spectacles 1006 is measured by the lens meter 1000. When this series of diagnostic interviews are finished, explanation of operational procedures of the optometric apparatus 2 is shown by movie on the display screen 64q' of the monitor device 64q.

And when the examinee sits down, places the jaw on the jaw receiver 6d and puts the forehead on the forehead receiver 6c, for auto-alignment for the left eye EL and the right eye ER of the examinee, the light source 36 for observing the anterior ocular segment, the illumination light source 48 for alignment and the liquid crystal display 53 in the body portions 5l and 5r are lighted.

The light of a fixation target displayed on the liquid crystal display 53 is projected to the fundus oculi Ef of the left eye EL and the right eye RL of the examinee through the reflecting mirror 54, the collimator lens 55, the reflecting mirror 56, the moving lens 57, the relay lenses 58 and 59, the reflecting mirror 60, the dichroic mirrors 61 and 39, the objective lens 38 and the prism P.

Figure 12:
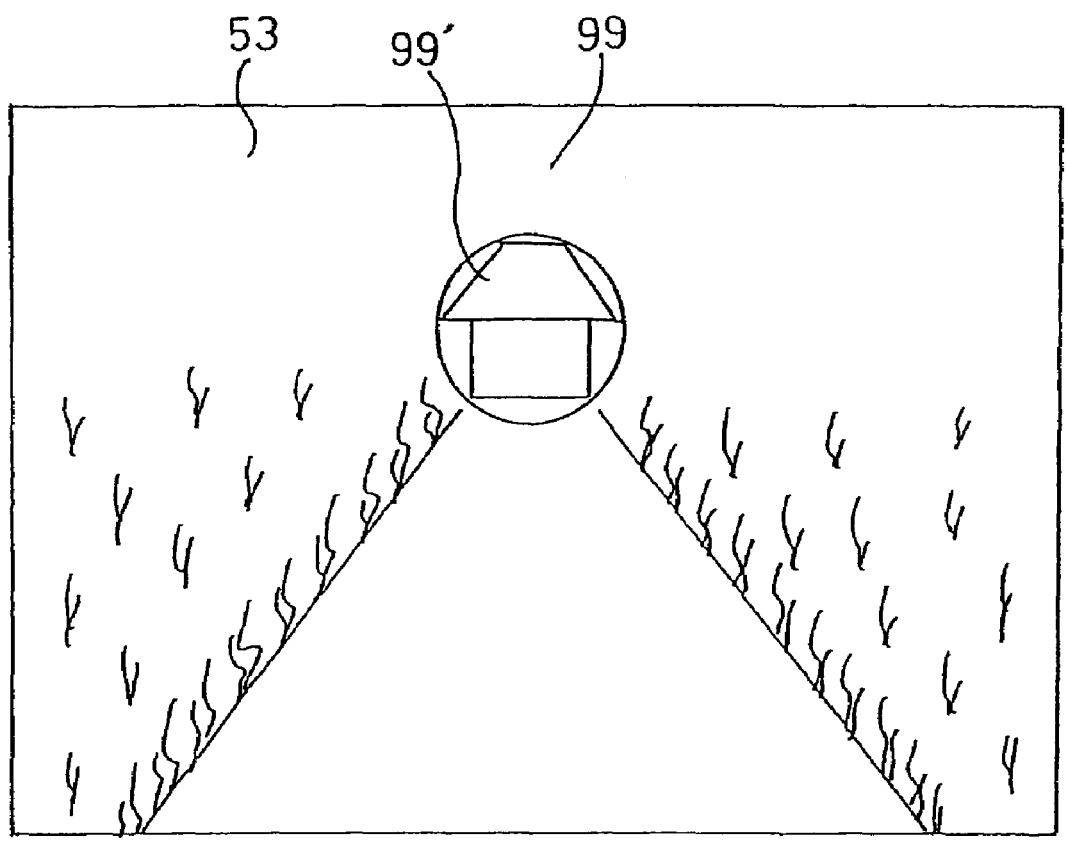
FIG. 12 is a view showing a landscape chart to be displayed on a liquid crystal display of the optical system shown in FIGS. 5 and 7.

On the liquid crystal display 53, a landscape chart 99 as a target is displayed, and the landscape chart 99 is presented to the examinee 4 as shown in FIG. 12.

Also, the operation control circuit 63 adjusts the body portions 5l and 5r in the right-and-left direction through initial setting so that the distance between centers of the prisms P and P (optical axes OL and OR) of the body portions 5l and 5r shall be an average distance between pupils of an adult examinee (PD value=66 mm). On the other hand, the examinee 4 adjusts the height of the jaw receiver and so on so that the examinee can see the landscape chart 99 as the fixation target.

Figure 13A:
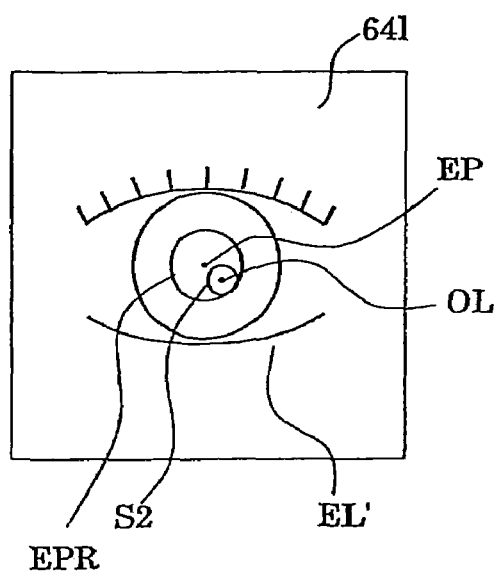
FIG. 13 is an explanatory view of an anterior ocular segment image displayed on a display screen of the liquid crystal display shown in FIG. 2, in which (a) is a view showing an anterior ocular segment image displayed on the display screen for the left eye and (b) is a view showing an anterior ocular segment image displayed on the display screen for the right eye.
Figure 13B:
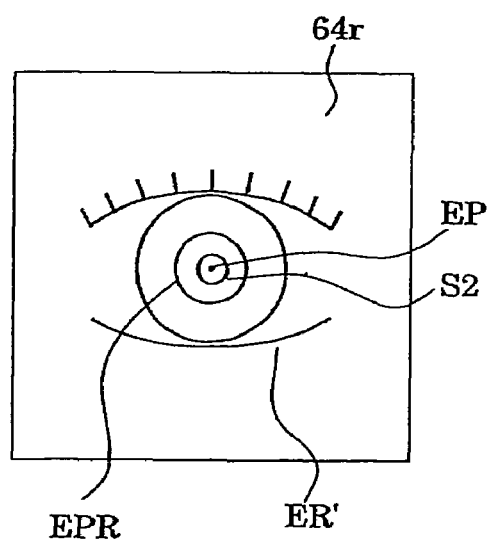

The illumination light from the light source 36 for illuminating the anterior ocular segment is projected to the anterior ocular segment of the left eye EL and the right eye RL through the diaphragm 36a and the projection lens 37, and the anterior ocular segment is illuminated. The reflected light from the anterior ocular segment of the left eye and the right eye is projected to the CCD (image pickup means) 46 through the prism P, the objective lens 38, the dichroic mirror 39, the diaphragm 40, the dichroic mirror 41, the relay lenses 42 and 43, the dichroic mirror 44 and the CCD lens (imaging lens) 45. And an anterior ocular segment image EL' of the left eye EL of the CCD 46 is imaged on the CCD 46. Also, the operation control circuit 62 displays an anterior ocular segment image EL' of the left eye EL on a liquid crystal display 64l of the body portion 5l as shown in FIG. 13(a) based on an output signal from the CCD 46. Similarly, an anterior ocular segment image ER' of the right eye ER is displayed on the liquid crystal display 64r of the body portion 5r as shown in FIG. 13(b).

In the meantime, alignment flux from the illumination light source 48 for XY alignment is projected to a cornea CL of the left eye EL of the examinee through the diaphragm 49 as the alignment target, the relay lens 50, the dichroic mirror 41, the diaphragm 40, the dichroic mirror 39, the objective lens 38 and the prism P. And the reflected light from the cornea CL is imaged on the CCD (image pickup means) 46 through the prism P, the objective lens 38, the dichroic mirror 39, the diaphragm 40, the dichroic mirror 41, the relay lenses 42 and 43, the dichroic mirror 44 and the CCD lens (imaging lens) 45, and a luminescent spot image EP from the cornea CL is formed on the CCD 46. Moreover, the operation control circuit 62 displays the luminescent spot image EP together with the anterior ocular segment image EL' of the left eye EL on the liquid crystal display 64l based on the output signal. Similarly, the luminescent spot image EP together with the anterior ocular segment image ER' of the right eye RL are displayed on the liquid crystal display 64r of the body portion 5r.

The operation control circuit 63 drives and controls the driving devices 20 and 26 so that the signal from the luminescent spot image EP from the CCD 46 enters a predetermined range S2 at the center of the CCD 46, that is, in the direction where the optical axis of the left eye EL of the examinee 4 matches the center of the prism P of the body portion 5l (optical axis OL). With this driving, the operation control circuit 63 stops operation of the driving devices 20 and 26 when the optical axis OL of the left eye EL of the examinee 4 enters the allowable range S2 almost matching the center of the prism P of the body portion 64l (optical axis OL) and completes the XY alignment for the left eye EL of the body portion 64l. The alignment for the right eye RL is the same as above.

The operation control circuit 63 drives and controls the Z (fore and aft) directional driving device 24 so that the luminescent spot image EP of the CCD 46 becomes clear when the XY alignment for the left eye EL of the body portion 5l is completed and moves and controls the body portion 64l in the direction of the optical axis OL (fore-and-aft direction). When it is detected that the luminescent spot image EP of the CCD becomes clear, the operation control circuit 46 stops driving of the Z (fore and aft) directional driving device 24, assuming that the Z alignment has been completed. The alignment in the Z direction for the right eye ER is the same as above. FIG. 13 shows the state where the luminescent spot image EP of the right eye ER enters the predetermined range S2 and the luminescent spot image EP of the left eye EL does not enter the predetermined range S2.

When the auto-alignment is completed, the operation control circuit 63 operates and controls the operation control circuit 62 of the body portion 64l and the operation control circuit 62 of the body portion 64r, respectively, lights the light sources 64 and 64 for measurement of the right and the left body portions 64l and 64r, respectively, injects infrared measurement flux from these light sources 64 and 64 for measurement and starts measurement of ocular refractivity of the left eye EL and the right eye ER of the examinee at the same time.

The flux from the light source 64 for measurement is projected to the fundus oculi Ef of the left eye EL and the right eye ER of the examinee 4 through the measurement flux projecting optical system 62. The measurement flux from the light source 64 for measurement is led to the ring target 67 through the collimator lens 65 of the body 51 and the conical prism 66. The ring-state measurement flux having passed the ring target 67 is projected to the fundus oculi Ef of the left eye EL and the right eye ER of the examinee through the relay lens 68, the ring-state diaphragm 69, the perforated prism 70 with the through hole 70*a* formed at the center, the dichroic mirrors 61 and 39, the objective lens 38 and the prism P.

The ring-state measurement flux projected to the fundus oculi Ef is reflected by the findus oculi Ef. This reflected light is imaged by the CCD 46 into a ring-state reflected image through the measurement flux light-receiving optical system 63, that is, the prism P, the objective lens 38, the dichroic mirrors 39 and 61, the through hole 70*a* of the perforated prism 70, the reflecting mirror 71, the relay lens 72, the moving lens 73, the reflecting mirror 74, the dichroic mirror 44, the CCD lens 45, etc.

A detection signal from this CCD 46 is inputted to the operation control circuit 62 of the body portion 64*l*. When the detection signal is inputted from the CCD 46, this operation control circuit 62 objectively measures ocular refractivity of the left eye EL and the right eye ER from the size and the shape of the ring-state reflected image imaged on the CCD camera 46.

Since details of measurement principle of this objective ocular refractive power is publicly known, its detailed description is omitted.

Hereinafter, how to use the optometric apparatus according to the present invention will be described.

1. Diagnostic interview is made while having the examinee 4 watch the display screen 64*q*' of the monitor device 64*q*.
2. Operational procedures of the optometric apparatus are displayed on the display screen 64' of the monitor device 64*q* and the operational procedures are explained with guidance in voice. After that, individual measurement is started when optometric measurement is selected.
3. Measurement of corrected visual acuity of a contact-lens wearer
    (1) When this measurement is selected, power-saving mode of the body portions 5*l* and 5*r* is canceled, simultaneously.
       The liquid crystal display (also called as the light source for target illumination) 53, the measurement light source (also called as LED) 64, the CCD camera 46 and so on are turned on.
    (2) The body is set to be initialized.
       The PD value shall be an average distance between pupils of 66 mm. The target shall be the landscape chart 99 shown in FIG. 12 for both eyes EL and ER.
    (3) With announcement of "Visual acuity when a contact lens is worn will be measured. Now, measurement method will be explained," characters are displayed on the display screen 64' of the monitor device 64*q*.
    (4) How to use the optometric apparatus 2 is played by movie on the monitor device 64*q* with voice.
       How to set on the face and how to operate the lever 6*h* which will be explained in the following is played by movie.
    (5) Then, voice guidance is given, saying "Now, visual acuity will be measured. Hold the lever 6*h* and look into the visual acuity tester with your contact lens on. Adjust the jaw receiver 6*d*. Can you see the picture of a house 99? If not, make adjustment so that you can see it."
    (6) The customer fixes the face with the jaw receiver 6*d* and the forehead receiver 6*c* and holds the lever 6*h*.
    (7) Auto-alignment function is started for both eyes at the same time.
    (8) The auto-alignment is repeated at the next step till alignment is matched, and finished when the alignment is matched.
        a) The number of auto-alignment times at the initial position shall be 2 retries and 3 times in total.
        b) If NG is given for both eyes at a) step, after announcement of "Position of the apparatus will be adjusted," an optical base (which is a base for each of the supports 5*p* and 5*q* and constitutes a part of a three-dimensional driving mechanism) is moved to the right by 5 mm while maintaining the PD value (L) of 66 mm.
        c) Auto-alignment is carried out 3 times.
        d) If NG is given for both eyes at c) step, after announcement of "Position of the optometric apparatus 2 will be adjusted," the position is moved to the left of the initial position by 5 mm while maintaining the PD value (L) of 66 mm.
        e) Auto-alignment is carried out 3 times.
        f) If NG is given for both eyes at e) step, after announcement of "Position of the apparatus will be adjusted," the position is moved to above the initial position by 5 mm while maintaining the PD value (L) of 66 mm.
        g) Auto-alignment is carried out 3 times.
        h) If NG is given for both eyes at g) step, after announcement of "Position of the apparatus will be adjusted," the position is moved to below the initial position by 5 mm while maintaining the PD value (L) of 66 mm.
        i) Auto-alignment is carried out 3 times.

Figure 14A:
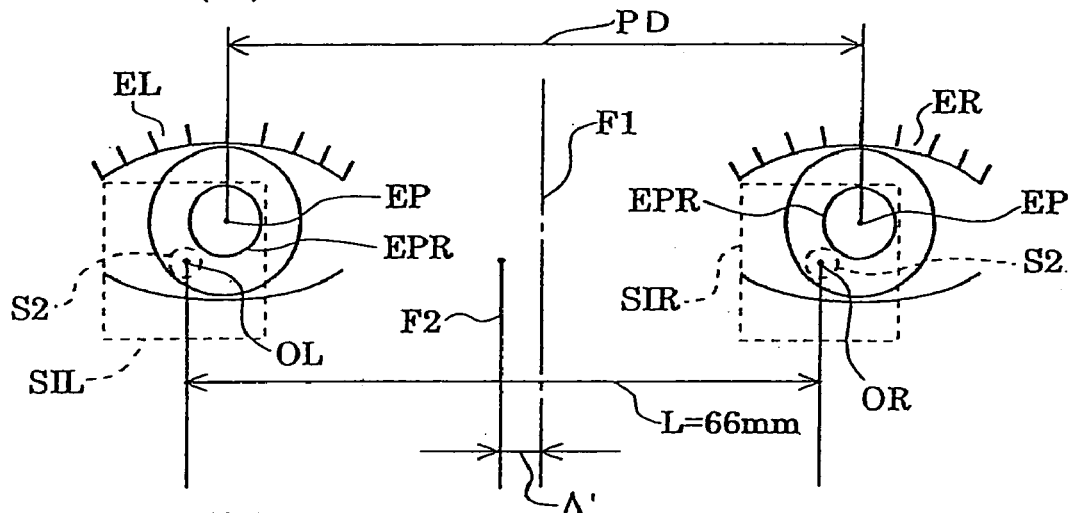
FIG. 14 is an explanatory view showing an example of auto-alignment, in which (a) shows the state where alignment is not gained, (b) shows the state where alignment is being gained and (c) shows the state where alignment is gained.
Figure 14B:
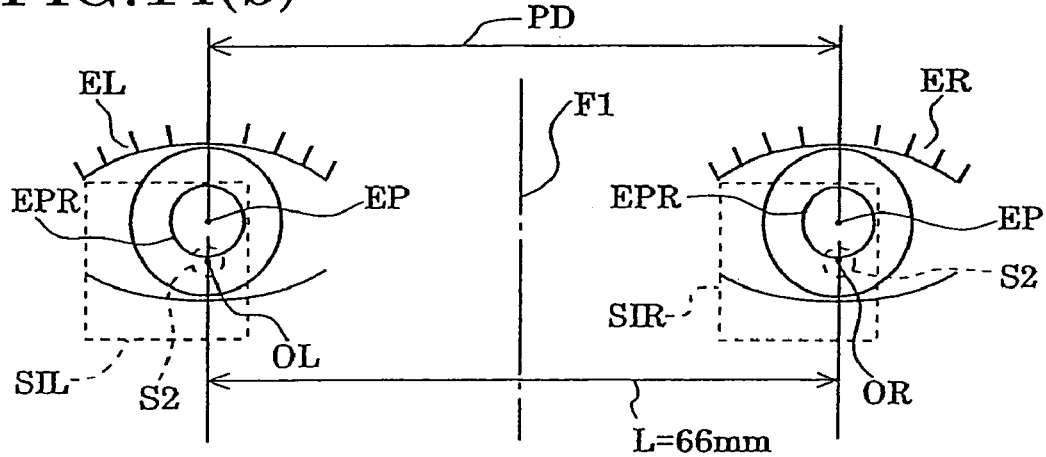
Figure 14C:
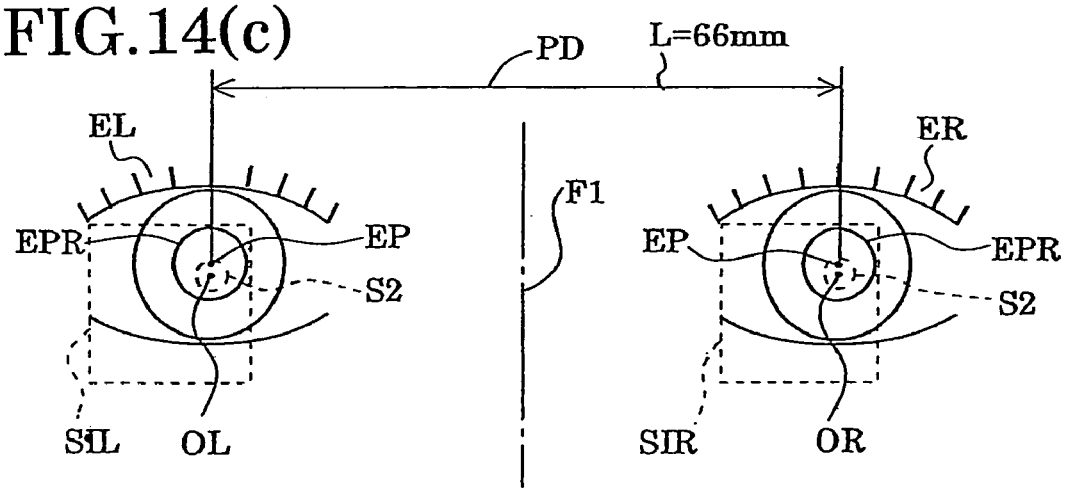
Figure 15A:
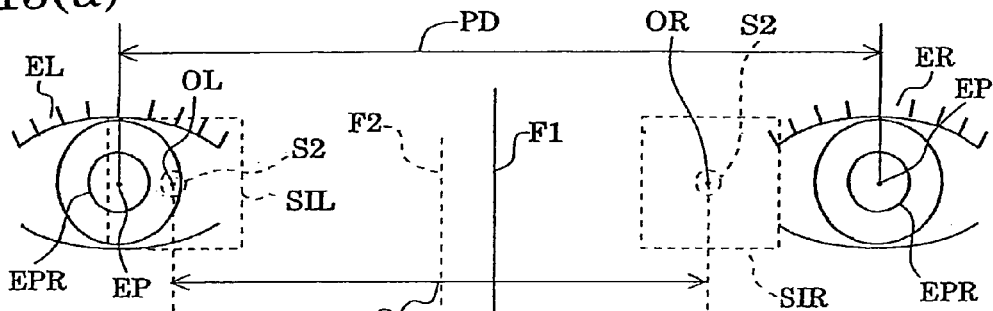
FIG. 15 is an explanatory view showing another example of auto-alignment, in which (a) shows the state where alignment is not gained, (b) shows the state where alignment is gained for the left eye, (c) shows the relation between the body portion and the eye to be examined when gaining alignment for the right eye using the data when the alignment is gained for the left eye and (d) shows the state where alignment is gained for both eyes.
Figure 15B:
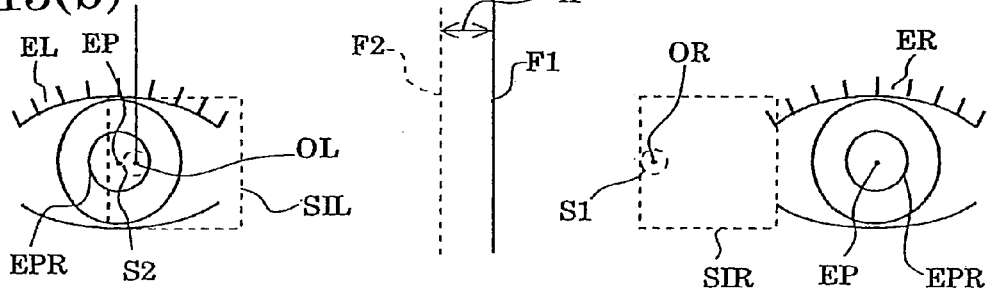
Figure 15C:
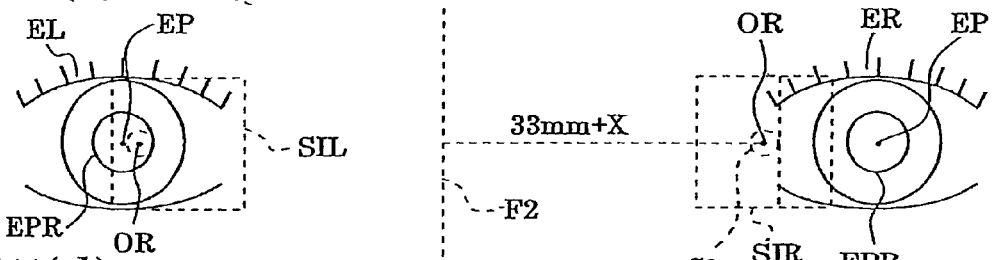
Figure 15D:
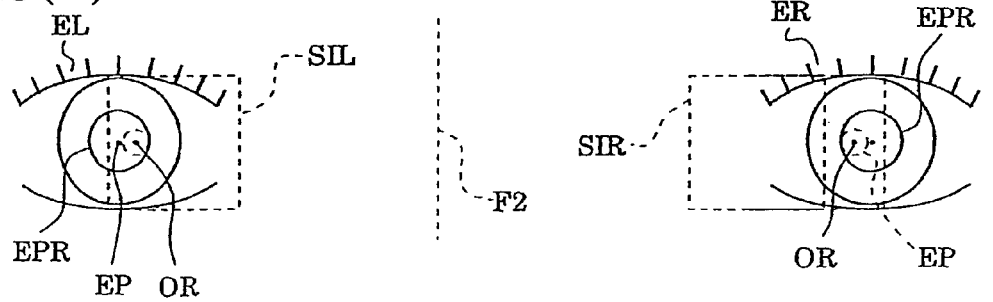

FIG. 14 shows an example of the procedures and this FIG. 14 show a positional relation of the optical axes OL and OR of the body portions 5*l* and 5*r* against the eyes EL and ER to be examined. In this FIG. 14, EPR is an actual pupil of the eyes EL and ER to be examined. Also, F1 is a midline of the face of the examinee 4 and F2 shows the position of an origin in the X direction of the body portions 5*l* and 5*r*. Δ' is a displacement amount between the midline and the origin position in the X direction. Moreover, SIL and SIR show moving ranges in the vertical and the horizontal directions of the body portions 5*l* and 5*r* at auto-alignment. FIG. 14(*a*) shows the state where the luminescent spot image EP is displaced diagonally above both for the right and the left eyes EL and ER. In this case, drive the body portions 5*l* and 5*r* to the right while maintaining the PD value at the initial value to have the state as shown in FIG. 14(*b*). And if the luminescent spot image EP is displaced from the predetermined range S2 even after that, the body portions 5*l* and 5*r* are driven in the upper or the lower direction. In the case shown in FIG. 14(*b*), since the luminescent spot image EP is displaced above, the body portions 5*l* and 5*r* are moved in the upper direction by 5 mm, for example, and the luminescent spot image EP enters the predetermined range S2 as shown in FIG. 14(*c*) and then, the auto-alignment is completed.

Thus, by combining the alignment procedures in (a) through (h) as appropriate, auto-alignment can be executed.

If the PD value of the spectacle lens is known in advance, this PD value is set as the initial value (initial amount) and a probability of success of auto-alignment in a short time can be further improved. Also, when the initial value of the PD value is set according to the age and sex of the examinee 4, the success probability of auto-alignment in a short time can be also improved.

Other than the above, auto-alignment can be made according to the procedures which will be explained hereinafter.

j) If alignment is gained for one of the eyes at any step of a) through i), y and z values are fixed and the y and z values for the eye for which alignment is gained are set for the y and z values for the NG'd eye and after announcement of "Position of the apparatus will be adjusted," the x value of the NG'd eye is enlarged by 5 mm.

For example, as shown in FIG. 15, when the PD value of the examinee 4 is unknown, and the PD value of the examinee 4 is larger than the average interpupillery distance L=66 mm, as shown in FIG. 15(*a*), there can be a case where even the auto-alignment moving ranges SIL and SIR of the body portions 5*l* and 5*r* can not cover.

In this case, for example, if the body portions 5*l* and 5R are moved to the left while maintaining the initial set value of the PD value (L=66 mm), as shown in FIG. 15(*b*), the luminescent spot image EP of the left eye EL enters the predetermined range S2, and auto-alignment for the left eye EL is achieved. The auto-alignment values (x, y, z) at this time are memorized.

And the initial set value of the PD value is cancelled, and the set value from the origin F2 of the body portion 5*r* is set to (33 mm+x), while maintaining the y and z values, and the body portion 5*r* is moved in the right-and-left direction within the range of the moving range SIR, as shown in FIG. 15(*c*). If it does not enter the predetermined range S2 even after executing this reciprocal movement in the right-and-left direction several times, the moving range SIR of the body portion 5*r* for the auto-alignment is further enlarged as shown in FIG. 15(*d*).

Then, the luminescent spot image EP enters the predetermined range S2, and therefore, when alignment is gained for one eye to be examined, the initial set value of the PD value is cancelled and the (x, y, z) values when alignment is gained for one eye to be examined are used as alignment data for the other eye to be examined, and auto-alignment is executed so as to further improve and accelerate alignment success probability.

k) Auto-alignment is carried out 3 times.

l) If NG is still given at the k) step, after announcement of "Position of the apparatus will be adjusted," the x value of the NG'd eye is further enlarged by 5 mm.

m) The steps j) through l) are repeated in the PD moving range.

n) At any of the steps a) through m) where alignment is gained, auto-alignment is finished, x, y, z positions are detected and the PD value is obtained.

(9) Measurement of corrected visual acuity of the right eye of a contact-lens wearer a) At the stage where alignment is gained, after announcement of "Do not narrow your eye," a target with the acuity value of 0.1 is presented to the right eye.

b) Next, the liquid crystal display (target illumination light source) 53 for the left eye is turned off.

c) Voice guidance is given, saying "Tilt the lever 6*h* in the direction of the cut in the target. If you can not see it, press the button 6*g* of the lever 6*h*."

d) The customer tilts the lever 6*h* in the direction of the cut in the Landolt ring.

e) It is determined if the presented target matches the direction in which the lever 6*h* is tilted.

f) After determining the direction of the cut in the Landolt ring and the direction in which the lever 6*h* is tilted, with the announcement of "How about this?" the next target is presented to the right eye.

(10) Algorithm to determine visual acuity is as explained as follows.

a) If the direction of the cut in the Landolt ring matches the direction in which the lever 6*h* is tilted, 1-step increase is made.

b) When NG is given during the increasing steps, presentation is made 4 times at the maximum.

c) During the steps of increasing the visual acuity value, if the direction of the cut is changed with the same acuity value, the horizontal direction and the vertical direction are presented alternately. Also, the right and left in the horizontal direction and up and down in the vertical direction are presented at random.

d) In the 4 presentations at the maximum, 2 NG's make the value below it assumed to be the acuity. 3 OKs are determined as that acuity value is held by the examinee, and 1-step increase is made.

e) As soon as the acuity value is determined, the liquid crystal display (illumination light source) 53 for the left eye is turned on, and the landscape chart 99 to be seen by both eyes is presented.

f) The acuity value is memorized.

(11) Measurement of corrected visual acuity of the left eye of a contact-lens wearer a) A target with the acuity value of 0.1 is presented to the left eye, and the target illumination light source for the right eye is turned off.

b) The same procedures to (9) c) through (10) d) are carried out.

c) As soon as the acuity value for the left eye is determined at the step (10) d), the target illumination light source for the right eye is turned on, and the landscape chart 99 for both eyes is presented.

4. Measurement of naked vision (right eye, left eye, both eyes)

(1) The power-saving mode of the body portions is canceled.

The chart illumination, the measurement LED, the CCD camera and so on are turned on.

(2) The body is set to be initialized.

The PD shall be 66 mm. The target shall be the landscape chart 99 for both eyes.

(3) Voice guidance is given, saying "Please look at the display screen (display screen 64*q'*). Now, measurement method will be explained."

(4) How to use the optometric apparatus is played by movie with voice.

How to set the face and how to operate the joystick lever 6*h* which will be explained in the following is played by movie.

(5) Then, voice guidance is given, saying "Now, optometry will be started. Hold the lever 6*h* and look into the visual acuity tester. Adjust the jaw receiver 6*d*. Can you see the picture of a house 99? If not, adjust it to a position where you can see it. Look into the tester so that you can see the chart at the center of the field of vision. When you are ready, press the button 6*g* of the lever 6*h*."

(6) The customer places the face on the jaw receiver 6d and the forehead receiver 6c and presses the button 6g of the lever 6h.
(7) Auto-alignment function is started for both eyes at the same time.
Then, the same operation as the measurement of the corrected visual acuity for a contact-lens wearer (9) is carried out.
(8) Measurement of the visual acuity of the right naked eye
   a) At the stage where alignment is gained, after announcement of "Do not narrow your eye," a target with the acuity value of 0.1 is presented to the right eye.
   b) Next, the target illumination light source for the left eye is turned off.
   c) Next, the same operation as the steps for measurement of corrected visual acuity for a contact-lens wearer (9) c) through (10) d) is carried out.
   d) The visual acuity value is memorized.
(9) Measurement of the visual acuity of the left naked eye.
   a) A target with the visual acuity value of 0.1 is presented to the left eye.
   b) The target illumination light source for the left eye is turned on, and the target illumination light source for the right eye is turned off.
   c) The same operation as the step (8) c) is carried out.
   d) As soon as the visual acuity value for the left eye is determined, the target illumination light source for the right eye is turned on and the landscape chart 99 is presented to both eyes.
   e) The visual acuity value is memorized.
(10) Optometry for both-eyes
   a) The visual acuity values of the right eye and the left eye measured at the step (8) and the step (9) are compared, and a target with the visual acuity value lower than the lower visual acuity value by 1 step is presented.
   b) If the direction in which the lever 6h is tilted matches the direction of the cut in the Landolt ring at the first presentation, the same steps as the measurement of corrected visual acuity for a contact-lens wearer (10) a) through d) are carried out.
   c) If the direction in which the lever 6h is tilted does not match the direction of the cut in the Landolt ring at the first presentation, the visual acuity value is lowered till OK
   d) At the OK stage, then, the visual acuity value is raised.
   e) If NG is given during the increasing steps, presentation is made 4 times at the maximum.
   f) During the steps of increasing the visual acuity value, if the direction of the cut is changed with the same acuity value, the horizontal direction and the vertical direction are presented alternately. Also, right and left in the horizontal direction and up and down in the vertical direction are presented at random.
   g) In the 4 presentations at the maximum, 2 NG's make the value below it assumed to be the acuity. 3 OKs are determined as that visual acuity value is held by the examinee, and 1-step increase is made.
   h) As soon as the visual acuity value is determined, the landscape chart 99 is presented to both eyes.
   i) The visual acuity value is memorized.
(11) Announcement is made, saying "Optometry with naked eyes is finished."

5. Optometry when spectacles are worn (right eye, left eye, both eyes)
   (1) Announcement is made, saying "Optometry when you are wearing glasses will be started."
   (2) S, C and A values obtained by measurement of dioptric power of spectacles are set.
   (3) A target with the visual acuity value 0.5 (the first target to be presented is not limited to 0.5. Arbitrary visual acuity values are chosen according to the eye to be examined. The same applies to the following) is presented to the right eye.
   (4) Then, the target illumination light source for the left eye is turned off.
      a) The customer tilts the lever 6h in the direction of the cut in the Landolt ring.
      b) It is determined if the presented target matches the direction in which the lever is tilted.
      c) After determining the direction of the cut in the Landolt ring and the direction in which the lever 6h is tilted, with the announcement of "How about this?" the next target is presented to the right eye.
   (5) Algorithm to determine visual acuity value is explained as follows.
      a) If the direction in which the lever is tilted matches the direction of the cut in the Landolt ring at the first presentation, the steps (10) (a) through (d) of the measurement for corrected visual acuity of a contact-lens wearer is followed.
      b) If the direction in which the lever is tilted does not match the direction of the cut in the Landolt ring at the first presentation, the visual acuity value is lowered till OK.
      c) At the OK stage, then, the visual acuity value is raised.
      d) If NG is given during the increasing steps, presentation is made 4 times at the maximum.
      e) During the steps of increasing the visual acuity value and changing the cut direction with the same visual acuity value, presentation is made in the horizontal direction and the vertical direction alternately. Also, right and left in the horizontal direction and up and down in the vertical direction are presented at random.
      f) In the 4 presentations at the maximum, 2 NG's make the value below it assumed to be the acuity. 3 OKs are determined as that acuity value is held by the examinee, and 1-step increase is made.
      g) As soon as the visual acuity value is determined, the landscape chart 99 is presented to both eyes.
      h) The visual acuity value is memorized.
   (6) Optometry for the left eye when spectacles are worn
      a) The visual acuity value 0.5 is presented to the left eye.
      b) The target illumination light source for the right eye is turned off at the same time.
      c) The same procedure as the optometry (4) a) through (5) g) when spectacles are worn.
      d) The visual acuity value is memorized.
   (7) Optometry for both eyes
      a) The illumination light source for the right eye is turned on, and the landscape chart 99 is presented to both eyes.
      b) The visual acuity values of the right eye and the left eye measured at the step (5) and the step (6) are compared, and a target with the visual acuity lower value than the lower visual acuity value by 1 step is presented to both eyes.

c) Next, measurement is made according to the optometry (4) a) through (5) g) for the right eye when spectacles are worn.
d) The visual acuity value is memorized.
e) The landscape chart 99 is presented to both eyes.
6. Objective refractive measurement
   (1) At the stage where 4. Measurement of naked vision or 5. Optometry when spectacles are worn is finished, the objective refractive measurement mode is automatically set.
      a) The landscape chart 99 is presented to both eyes as a target.
      b) PD shall be the PD value previously obtained.
   (2) Announcement is made, saying "Necessary dioptric power of the spectacles will be obtained. Please look into the optometric machine." Then, announcement is made, saying "Please blink several times." After 1 second, announcement is made, saying "Please keep your eyes wide open and do not blink for some time."
   (3) Auto-alignment is made for both eyes at the same time.
   (4) Simultaneous objective measurement is made for both eyes.
   (5) Representative values of display of S, C and A data are displayed/outputted.
7. Optometry based on objective refractive measurement results (right eye, left eye, both eyes)
   (1) Optometry for the right eye
      a) When the objective measurement for both eyes is completed, announcement is made, saying "Refractive measurement values were obtained. Optometry will be made by these refractive measurement values."
      b) S, C and A values obtained by objective refractive measurement are set for both eyes.
      c) A target with the visual acuity value of 0.5 is presented to the right eye.
      d) At the same time, the target illumination light source for the left eye is turned off.
      e) Announcement is made, saying "Please tilt the lever 6h in the direction of the cut in the target."
      f) The same measurement as the optometry (4) a) through (5) g) when spectacles are worn is made in the following.
      g) The visual acuity value is memorized.
   (2) Optometry for the left eye
      a) The S, C and A values for the left eyes are set for the objective refractive measurement values.
      b) The illumination for the left eye is turned on, while the illumination for the right eye is turned off
      c) A target with the visual acuity value of 0.5 is presented to the right eye.
      d) Announcement is made, saying "Please tilt the lever 6h in the direction of the cut in the target."
      e) The same procedures as the optometry (4) a) through (5) i) when spectacles are worn are carried out.
      f) The visual acuity value is memorized.
   (3) Optometry for both eyes
      a) The illumination for the right eye is turned on.
      b) The objective refractive measurement value is set for both eyes.
      c) The objective refractive measurement values of the right eye and the left eye based on the objective refractive measurement are compared, and a target with the visual acuity value lower than the lower visual acuity value by 1 step is presented.
      d) Announcement is made, saying "Please tilt the lever 6h in the direction of the cut in the target."
      e) The same procedures as the optometry (4) a) through (5) g) when spectacles are worn are carried out.
      f) The visual acuity value is memorized.
      g) The landscape chart 99 is presented to both eyes.
8. Precision determination of spherical dioptric power by R & G test (red and green test) and optometry (right eye, left eye)
   (1) Red/green chart for binocular balance
   FIG. 16 shows an example of the red/green chart for binocular balance, in which FIG. 16(*a*) shows a target 70A of the red/green chart for the left eye and FIG. 16(*b*) shows a red/green chart 70B for the right eye, and FIG. 16(*c*) shows how the targets 70A and 70B are seen when seen by both eyes with emmetropia.
   (2) How the target is seen
      a) Right eye: A numeral target "9" with the upper side in the visual field of green and a numeral target "6" with the lower side in the visual field of red.
      b) Left eye: A numeral target "3" with the left side in the visual field of green and a numeral target "5" with the right side in the visual field of red ((3) S, C and A values obtained in the objective refractive measurement are set for both eyes).
   (4) R & G test for the right eye
      a) The red/green chart for binocular balance is presented.
      b) For the left eye, the illumination light source is turned off at the same time the target is presented.
   (5) Announcement is made, saying "Please open your eyes widely."
   (6) Auto-alignment is carried out for both eyes at the same time.
   (7) A question is made in voice, saying "Are the red and green targets seen in the same way? Or either of which is clearer?"
   (8) Announcement is made, saying "If you see them in the same way, please press the button 6g of the lever 6h. If they are seen differently, please tilt the lever 6h in the direction seen more clearly."
      a) If the lever 6h is tilted in the upper side (green is seen more clearly), +0.25D is added to the spherical dioptric power, and announcement is made, saying "Are the red and green targets seen in the same way? Or either of which is clearer?"
      b) If the lever 6h is tilted in the lower side (red is seen more clearly), −0.25D is added to the spherical dioptric power, and announcement is made, saying "Are the red and green targets seen in the same way? Or either of which is clearer?"
   (9) How to determine spherical dioptric power
      a) When the button 6g of the lever 6h is pressed, it is finished with the D value at that time.
      b) After the lever 6h is tilted in the upper side (green) and S+0.25 is added, when the lever 6h is tilted in the lower side (red), it is finished with the D value at that time.
      c) After the lever 6h is tilted in the lower side (red) and S−0.25 is added, when the lever 6h is tilted in the upper side (green), it is finished with the D value with S+0.25D added.
   (11) Optometry for the right eye after the R & G test
      a) As soon as the spherical dioptric power is determined, the visual acuity value of 0.5 is presented.
      b) Announcement is made, saying "Please tilt the lever 6h in the direction of the cut of the target."

c) The same measurement as the optometry (4) a) though (5) i) when spectacles are worn is carried out in the following.

d) The D value and the visual acuity value for the right eye are memorized.

(10) R & G test for the left eye, optometry a) The target illumination light source for the left eye is turned on, while the target illumination light source for the right eye is turned off.

b) The left eye views a numeral target "3" in the green visual field and a numeral target "5" with the right side in the red visual field.

c) After that, description in 8. (5) through (10) c) is followed with replacement of "upper" by "left" and "lower" by "right."

d) As soon as the visual acuity value is determined, the illumination light source for the right eye is turned on, and the landscape chart 99 is presented to both eyes.

e) The D chart and the visual acuity value for the left eye are memorized.

9. Astigmatic test

If the visual acuity value obtained by 8. R & G test result (10) d) or (11) e) is less than 0.7, a check test is made to see if astigmatism is corrected or not.

Figure 17:
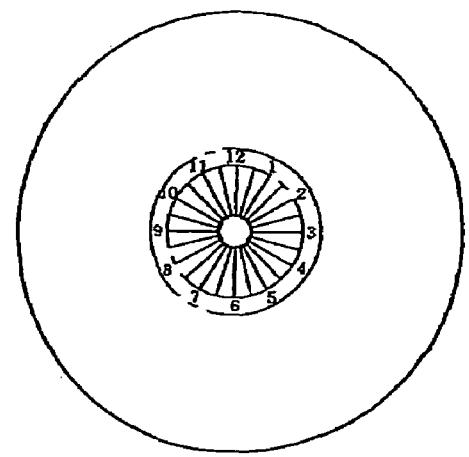
FIG. 17 is a view showing an example of an astigmatic chart.

For this, the astigmatic test chart shown in FIG. 17 is used.

(1) It is determined if the visual acuity values of the left eye and the right eye are less than 0.7 or not. In the case of only one of them, a check test is made to see astigmatism is corrected or not for the eye in the order of the right eye and then, the left eye, if the values of both eyes are less than 0.7. In the following, description is made for the case where the visual acuity value for the right eye is less than 0.7.

(2) Astigmatic test for the right eye:

Announcement is made, saying "Astigmatic test will be made. The astigmatic test will be explained."

(3) How to use the apparatus is played with voice by movie.

(4) Announcement is made, saying "Measurement will be started. Hold the lever 6h and look into the optometric machine."

(5) Announcement is made, saying "Are all the lines seen equally? If so, tilt the lever 6h to the front, and if there is any bold line, tilt the lever 6h to the back."

(6) If tilted to the front (seen equally), the visual acuity value of 0.5 is presented.

a) Announcement is made, saying "Tilt the lever in the direction of the cut of the target."

b) The same procedure in 5. Optometry when spectacles are worn (4) a) through (5) g).

c) The visual acuity value is determined.

(7) Comparison is made with the visual acuity value obtained in 8. R & G test (10) d) or (11) e).

a) If the visual acuity value is the same or the present visual acuity value is better, the present visual acuity value is set as the visual acuity value of the customer.

b) If the visual acuity value obtained in 8. R & G test (10) d) or (11) e) is better, the value obtained in 8. R & G test (10) d) or (11) e) is set as the visual acuity value of the customer.

c) The D value and the visual acuity value are memorized.

(8) If the lever 6h is tilted to the back (not equal but there is a bold line.), the visual acuity value obtained in 9. R & G test (10) d) or (11) e) is set as the visual acuity value of the customer. In this case, a comment that "A bold line remains in the astigmatic test." is given on the display of the 18. Measurement result, which will be described later. Or it returns to 6. Objective refractive measurement.

10. Cross cylinder test (hereinafter referred to as CC test)

Figure 18:
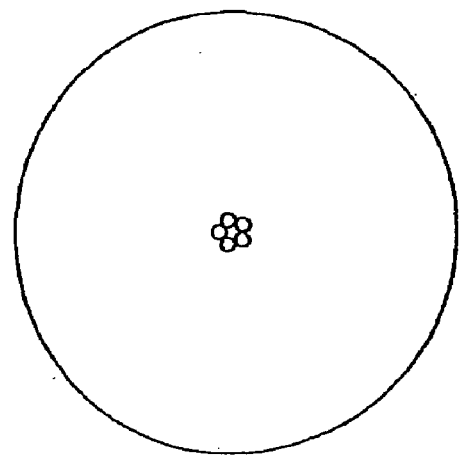
FIG. 18 is a view showing an example of a cross-cylinder chart.

The cross cylinder chart shown in FIG. 18 is used.

10-1. Precision determination method of cylinder axis 10-1-1. Precision determination procedure of cylinder axis in general subjective Refractive Measuring Method An intermediate axis of a cross cylinder lens ±0.5D is set to the cylinder axis obtained roughly, and the intermediate axis is reversed as a rotational axis. How both of them are seen by reversal is compared, and always on the better side, both the cylinder axis obtained by the outline and the intermediate axis of the cross cylinder lens are rotated by 50 in the direction of the negative axis of the cross cylinder lens. By repeating this, an angle where there is no difference between both sides by reversal in how they are seen is obtained, and it shall be set as an accurate astigmatic dioptric power. 10-1-2. Application example of an embodiment of the present invention.

The refractivity obtained by the R & G test is set as $D\theta, 1$ ($S_1, C_1, A_1$), the refractivity of the cross cylinder lens ±0.5D as $D\theta, 2$ ($S_2, C_2, A_2$) and the synthetic refractivity of $D\theta, 1$ and $D\theta, 2$ as $D\theta, 0$ ($S_0, C_0, A_0$).

Since the intermediate axis of $D\theta, 2$ is set to the cylinder axis $A_1$ of $D\theta, 1$, and reversed with the intermediate axis as the rotational axis, there is a relation of $A_2 = A_1 \pm 45°$ between the axial angles $A_1$ and $A_2$ of $D\theta, 1$ and $D\theta, 2$.

Here, the synthetic refractivity $D\theta, 0$ ($S_0, C_0, A_0$) of the $D\theta, 1$ and $D\theta, 2$ is obtained from the following formula.

Numeral 1

(1) General formula $$S_0 = \left(S_1 + S_2 + \frac{C_1 + C_2}{2}\right) - \frac{C_0}{2} \quad (a)$$

$$C_0 = \pm \sqrt{(C_1^2 + C_2^2 + 2C_1C_2\cos 2(A_1 - A_2))} \quad (b)$$

$$A_0 = \frac{1}{2}\tan^{-1}\frac{C_1\sin 2A_1 + C_2\sin 2A_2}{C_1\cos 2A_1 + C_2\cos 2A_2} \quad (c)$$

10-1-3. Precision determination procedure of cylinder axis (1) The landscape chart 99 is presented to both eyes.

(2) Announcement is made, saying "Precision measurement of cylinder axis will be started. Two visions will be compared. If the first "1" is seen better, tilt the lever 6h to the left, while if the next "2" is seen better, tilt the lever 6h to the right. If the visions are the same, press the button 6g of the lever 6h."

(3) The target illumination light source for the left eye is turned off.

(4) The target for both eyes is switched to CC chart.

(5) −0.5D is temporarily added to the spherical dioptric power S1 of both eyes.

(6) Precision determination of cylinder axis of the right eye a) The target illumination light source for the right eye is turned off, and the synthetic refractivity $D\theta, 0$ ($S_0, C_0, A_0$) of $D\theta, 1$ and $D\theta, 2$ when $A_2 = A_1 + 45°$ is set. Hereinafter, this state is referred to as (A+).

b) The target illumination light source for the right eye is turned on, "Between how this "1" is seen and" is uttered, and (A+) is presented.

c) The target illumination light source for the right eye is turned off, and the synthetic refractivity $D\theta, 0$ ($S_0, C_0,$ A0) of Dθ, 1 and Dθ, 2 when A2=A1−45° is set. Hereinafter, this state is referred to as (A−).
d) The target illumination light source for the right eye is turned on, "how this "2" is seen, which is seen better?" is uttered, and (A−) is presented.
e) (A+) is presented, a sequence that ""1", and" is uttered, (A−) is presented and ""2." How about it?" is repeated.
f) If the lever 6h is tilted to the left, it is assumed that A1=A1+5°, while if tilted to the right, it is assumed that A1=A1−5°. Naturally, A2 is changed according to that.
g) If the button 6g of the lever 6h is pressed, the angle at that time shall be the final axial angle. If the lever 6h is tilted in the opposite direction such that (A+) to (A−) or (A−) to (A+), an average value of both angles shall be the final axial angle.

(7) Precision determination of cylinder axis of the left eye
a) The target illumination light source for the right eye is turned off.
b) The synthetic refractivity Dθ, 0 (S0, C0, A0) of Dθ, 1 and Dθ, 2 when A2=A1+45° is set for the left eye. Hereinafter, this state is referred to as (A+).
c) The target illumination light source for the left eye is turned on, "Between how this "1" is seen and" is uttered, and (A+) is presented.
d) The following procedure shall be the same as steps in (6) c) through g) with the "right eye" reading as the "left eye."

(8) When the final axial angle for the left eye is determined, the target illumination light source for the left eye is turned off.

10-2. Precision determination of astigmatic dioptric power
10-2-1. Precision determination procedure of cylinder axis in general subjective refractivity measuring method A negative axis or a positive axis of the cross cylinder lenses 59A and 59B is matched to the axis of a cylindrical lens of the body and reversed with the intermediate axis as the rotational axis, as with the precision determination of the cylinder axis, and the visions of both eyes are compared. If there is less flow in an image when the negative axis of the cross cylinder lenses 59A and 59B is matched to the axis of the cylindrical lens of the body, C−0.25D is added. In the meantime, if there is less flow in an image when the positive axis is matched to axis of the cylindrical lens of the body, C−0.25D is subtracted. In this way, visions in both sides are compared by reversal, and the weaker cylindrical lens power is determined as the final cylinder axis according to the principle that the cylindrical lens power when visions seem the same in both sides, or if there is a slight difference, the weakest negative power is selected.

10-2-2. Application example of an embodiment of the present invention

The refractivity obtained by the objective refractive measurement shall set as Dθ, 1 (S1, C1, A1), the refractivity of the cross cylinder lens ±0.5D as Dθ, 2 (S2, C2, A2) and the synthetic refractivity of Dθ, 1 and Dθ, 2 as Dθ, 0 (S0, C0, A0).

Since the negative axis or the positive axis Dθ, 2 is set o the cylinder axis A1 of Dθ, 1, and reversed with the intermediate axis as the rotational axis, there is a relation of A2=A1±90° between the axial angles A1 of Dθ, 1 and Dθ, 2 and A2 of the cross cylinder axis.

Two ways of synthetic refractivity Dθ, 0 (S0, C0, A0) of Dθ, 1 and Dθ, 2 are obtained.

10-2-3. Precision determination procedure of astigmatic dioptric power
(1) Announcement is made, saying "Precision measurement of astigmatic dioptric power axis will be started. Two visions will be compared. If the first "1" is seen better, tilt the lever 6h to the left, while if the next "2" is seen better, tilt the lever 6h to the right. If the visions are the same, press the button 6g of the lever 6h."

(2) Precision determination of astigmatic dioptric power for the right eye
a) The synthetic refractivity Dθ, 0 (S0, C0, A0) of Dθ, 1 and Dθ, 2 when A2=A1+90° is set. Hereinafter, this state is referred to as (P+).
b) The target illumination light source for the right eye is turned on, "Between how this "1" is seen and" is uttered, and (P+) is presented.
c) The target illumination light source for the right eye is turned off, and the synthetic refractivity Dθ, 0 (S0, C0, A0) of Dθ, 1 and Dθ, 2 when A2=A1 is set. Hereinafter, this state is referred to as (P−).
d) The target illumination light source for the right eye is turned on, "how this "2" is seen, which is seen better?" is uttered, and (P−) is presented.
e) (P+) is presented, a sequence that ""1" and" is uttered, (P−) is presented and ""2." How about it?" is repeated.
f) If the lever 6h is tilted to the left, {1: (P+)}, +0.25D is added to C1, while if tilted to the right, {2: (P−)} and −0.25D is added to C1.
g) If the button 6g of the lever 6h is pressed, the angle at that time shall be the final astigmatic dioptric power.
h) If the lever 6h is tilted to the right after the lever 6h is tilted to the left and +0.25D is added to C1, the astigmatic dioptric power at that time shall be the final astigmatic dioptric power. On the contrary, if the lever 6h is tilted to the left after the lever 6h is tilted to the right and −0.25D is added to C1, +0.25D is added to C1, and this value shall be the final astigmatic dioptric power.

(3) Precision determination of astigmatic dioptric power for the right eye.
a) The target illumination light source for the right eye is turned off.
b) The synthetic refractivity Dθ, 0 (S0, C0, A0) of Dθ, 1 and Dθ, 2 when A2=A1+90° is set for the left eye. Hereinafter, this state is referred to as (P+).
c) The target illumination light source for the left eye is turned on, "Between how this "1" is seen and" is uttered, and (P+) is presented.
d) The same procedure as the steps in 10-2-3. (2) c) through h) are executed in the following.

(4) The target illumination light source for the left eye is turned off. The illumination is turned off for both eyes.
(5) Except the cross cylinder lens ±0.5D, A'1 obtained by the precision determination procedure for the cylinder axis in 10-1-3 is set and C'1 obtained by the precision determination procedure for the astigmatic dioptric power in 10-2-2 is set for both eyes.
(6)-0.50D added in the step (5) in 10-1-3 is subtracted.
(7) The landscape chart 99 is presented to both eyes, and the target illumination light source for both eyes is turned on.

11. Binocular balance test
(1) How the target is seen
 a) Right eye: A numeral target "9" with the upper side in the visual field of green and a numeral target "6" with the lower side in the visual field of red.
 b) Left eye: A numeral target "3" with the left side in the visual field of green and a numeral target "5" with the right side in the visual field of red.
 c) Both eyes: 4 numeral targets arranged in the form of a rhomboid in the green or red vision in the vertical and horizontal directions.
(2) How to measure
 a) S, C and Avalues obtained by 9. CC test are set.

b) The binocular balance chart is set respectively for the right eye and the left eye.
c) Announcement is made, saying "Are the 4 numerals seen equally clearly? Or is there any difference in how they are seen?"
d) Announcement is made, saying "If the 4 numerals are seen equally clearly, press the button 6g of the lever 6h. If there is any difference in how they are seen, tilt the lever 6h in the direction of the most clearly seen numeral."
e) After the lever 6h is tilted, announcement is made again, saying "Tilt the lever 6h in the direction of the second clearly seen numeral."
f) Processing is made following the list below according to the direction where the lever 6h is tilted in the steps d) and e).

TABLE 1

| Direction where the lever is tilted first time | Direction where the lever is tilted next | Action |
|---|---|---|
| ① Down(Right Eye, Red Field) | Right(Left Eye, Red Field) | Binocular balance is good. |
| Right(Left Eye, Red Field) | Down(Right Eye, Red Field) | Finished. |
| ② Up(Right Eye, Green Field) | Left(Left Eye, Green Field) | Overcorrection for both eyes. |
| Left(Left Eye, Green Field) | Up(Right Eye, Green Field) | S + 0.25 D is added to both eyes. |
| ③ Down(Right Eye, Red Field) | Left(Left Eye, Green Field) | Left eye is somewhat overcorrected. |
| Left(Left Eye, Green Field) | Down(Right Eye, Red Field) | S + 0.25 D is added to the left eye. |
| ④ Up(Right Eye, Green Field) | Right(Left Eye, Red Field) | Right eye is somewhat overcorrected. |
| Right(Left Eye, Red Field) | Up(Right Eye, Green Field) | S + 0.25 D is added to the right eye. | g) Other than ① in the list in f), return to the step b) after correction of spherical dioptric power according to respective action.
h) The sequence is repeated till the button 6g of the lever 6h is pressed in d) or ① in f) is reached.

12. Optometry by binocular balance test
(1) Setting of S, C and A values
a) The S, C and A values obtained by binocular balance test are set for both eyes.
b) Announcement is made, saying "Dioptric power of spectacles recommended for you was obtained. Then, optometry will be made with this spectacle dioptric power."
(2) Optometry is carried out for the right eye, left eye and both eyes 13. Check of the Optometric Results
13-1. For those Wearing Spectacles
(1) Announcement is made, saying "Vision with naked eyes, that with the present spectacles and that with the spectacles recommended for you will be shown."
(2) Every time, the measurement result shown to the customer is indicated by a white line or a white square on the display screen 64q' of the monitor device 64q.
(3) Announcement is made, saying "Vision with naked eyes will be shown."
(4) S and C values are set to 0D for both eyes, and the customer is made to gaze the landscape chart 99 for 3 seconds, for example.
(5) Announcement is made, saying "Next, vision with the currently used spectacles will be shown."
(6) If dioptric power of the spectacles was measured, S, C and A values are set to the dioptric power measurement value of the spectacles, and the customer is made to gaze the target for 3 seconds, for example.
(7) Announcement is made, saying "With the spectacles recommended for you this time, you can see like this."
(8) The S, C and A values (recommended refractivity) by the results of 11. Binocular balance test are set, and the customer is made to gaze the target for 3 seconds, for example.
(9) Announcement is made, saying "With the spectacles recommended for you this time, you can see like this. If this vision which is generally easy to see and hard to be tired is OK, please press the button 6g of the lever 6h," and it is presented for 4 seconds, for example. If the lever 6h is pushed during this 4-second period, the recommended refractivity is set as the selected refractivity and finished.
(10) If the button 6g of the lever 6h is not pressed during the 4 seconds, announcement is made, saying "If you want to check how you can see with the currently used spectacles, please tilt the lever 6h to the right," and it is presented for 4 seconds, and if the lever 6h is not operated for the 4 seconds, the recommended refractivity is set as the selected refractivity and finished.
(11) If the lever 6h is tilted to the right during the 4 seconds, the dioptric power of the spectacles is set for both eyes, and announcement is made, saying "This is how you see with the currently used spectacles. If this is OK for you, please press the button 6g of the lever 6h," it is presented for 4 seconds. If the button 6g of the lever 6h is pressed during this 4-second period, the dioptric power of the spectacles is set as the selected refractivity and finished.
(12) If the button 6g of the lever 6h is not pressed during the 4 seconds, announcement is made, saying "If you want to check how you can see with the spectacles recommended fro you, please tilt the lever 6h to the left," and it is presented for 4 seconds, and if the lever 6h is not operated for the 4 seconds, the recommended refractivity is set as the selected refractivity and finished.
(13) At the same time as finish, the selected refractivity is set for both eyes.
(14) Either of the "spectacles dioptric power" or "recommended refractivity" selected as the selected refractivity is shown in red characters of 19. Display of measurement results, which will be mentioned later.

13-2. For those who wear contact lenses and those who do not wear spectacles or contact lenses (1) Announcement is made, saying "How you can see with your naked eyes and with the spectacles recommended for you are shown."
(2) Every time, the measurement result shown to the customer is indicated by a white line or a white square on the display screen 64q' of the monitor device 64q.
(3) Announcement is made, saying "Vision with naked eyes will be shown."
(4) S and C values are set to 0D for both eyes, and the customer is made to gaze the landscape chart 99 for 3 seconds.
(5) Announcement is made, saying "With the spectacles this time, you can see like this."
(6) The S, C and A values by the results of 11. Binocular balance test (hereinafter referred to as recommended refractivity) are set and the customer is made to gaze for 3 seconds.
(7) The recommended refractivity is set as the selected refractivity and finished.
(8) The "recommended refractivity" selected as the selected refractivity is shown in red characters by 18. Display of measurement results.

14. Cross heterophoria test

FIG. 19 shows an example of a cross heterophoria test chart, in which FIG. 19(*a*) shows a target 71A of the cross heterophoria test chart for the left eye, FIG. 19B shows a target 71B of the cross heterophoria test chart for the right eye, and FIG. 19(*c*) shows how the targets 71A and 71B are seen by normal binocular visions. Table 2 shows how the heterophoria is seen.

TABLE 2

| How it is seen | Heterophoria | Prescription |
|---|---|---|
| ⊢ (cross, aligned) | Orthotopic | |
| ⊢ (right-shifted) | Estophoria | BO (base-out) prism is added. |
| ⊢ (left-shifted) | Exophoria | BI (base-in) prism is added. |
| ⊢ (up-shifted) | Left-eye hyperphoria | BU (base-up) prism is added to the right eye. BD (base-down) prism is added to the left eye. |
| ⊢ (down-shifted) | Right-eye hyperphoria | BD prism is added to the right eye. BU prism is added to the left eye |

(1) How to measure a) The cross heterophoria chart shown in FIG. 19 is set for both eyes.

Figure 7:
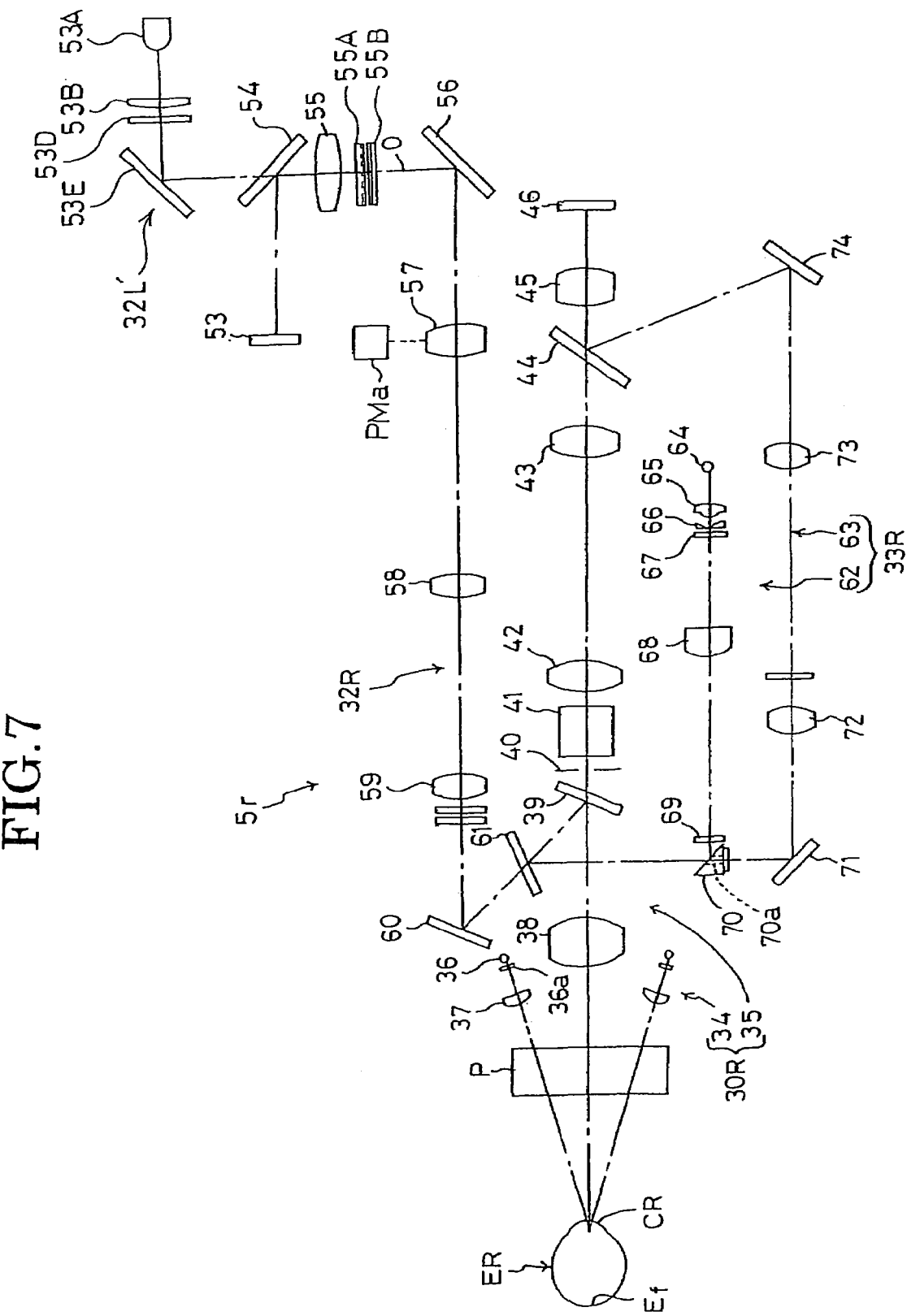
FIG. 7 is a plan view of the optical system for the right eye shown in FIG. 6.

At this time, the LED 53A shown in FIGS. 5 and 7 are lighted, and a fusion frame 53F is shown respectively to both eyes.

The reason will be explained below.

There are heterophoria and heterotropia in ocular deviation. The heterophoria is an ocular deviation in which both eyes are oriented properly to an object to be gazed in a daily private life and binocular single vision is made all the time, but when one eye is covered, the line of vision is slightly deviated, while the heterotropia is an ocular deviation in which whether one eye is covered or not, the line of vision is deviation all the time, and the object to be gazed is diplopia all the time.

When a person who has heterophoria, not heterotropia, gazes an object in the natural world, the object does not become diplopia but it is seen overlapped, which does not hinder daily life. However, if the optical system for the left eye and the optical system for the right eye are provided separately, and such an optical system is employed that a target for the left eye is presented to the left eye and the target for the right eye is presented to the right eye through each of the optical system, differently from watching objects in the natural world, when a person with heterophoria sees each of the targets with both eyes, when the target seen by the left eye is different from the target seen by the right eye, the target seen by the left eye might not match the target seen by the right eye.

Also, even if the target presented to the left eye is the same as the target presented to the right eye, in the case of optometry with a one-letter target with a narrow visual field or near optometric test with further convergence, the target seen by the left eye can not be fused with the target seen by the right eye in some cases.

Anyone can have more or less heterophoria, but normal binocular vision is made in the daily life. The cross heterophoria test in the form of the embodiment of the present invention presents a fusion frame in such a manner that a target presented to the left eye and the target presented to the right eye are surrounded, and its object is to extract examinees who can not fuse images even if there is a fusion frame, which brings about abnormality in daily binocular vision function. Also, in the case of optometry, a fusion frame is presented, and an examinee who does not have any trouble in daily life even if he/she has heterophoria can make binocular vision easily.

b) Announcement is made, saying "Can you see the 4 lines? If so, please press the button 6g of the lever 6h. If you see only horizontal 2 lines, tilt the lever 6h to the right or left, and if you see only vertical 2 lines, tilt the lever 6h to the front or back."

c) If the lever 6h is tilted to the right or left, suppression is acting on the right eye, and if tilted to the front or back, the suppression is acting on the left eye, and the heterophoria test is not possible. "Heterophoria: Requires close examination" is memorized and the examination is finished.

d) If the button 6g of the lever 6h is pressed, announcement is made, saying "Are the centers of the horizontal line and the vertical line overlapped? If overlapped, press the button 6g of the lever 6h. If the vertical line is on the right hand side, tilt the lever 6h to the right, and if on the left, tilt the lever 6h to the left."

e) If the button 6g is pressed, "Heterophoria: Normal" is memorized and the heterophoria test is finished. If the lever 6h is tilted to the right, BO prism is set for both eyes at the same time, while if tilted to the left, BI prism is set for both eyes at the same time. The minimum unit of prism conversion shall be 0.5 Δ.

f) If the lever 6h is tilted to the right, announcement is made, saying "Tilt the lever 6h to the right or left till the vertical line matches the center position of the horizontal line, and when matched, press the button 6g of the lever 6h.

g) Until the button 6g of the lever 6h is pressed, the number of times that the lever 6h is tilted to the right or left is counted. If the lever is tilted to the left after being tilted to the right, it makes 0 times on balance. The right is BO (esophoria), the left is BI (exophoria) and the number of times being tilted ×0.5 is a prism amount (Δ).

h) For the horizontal heterophoria, "BO (or BI) Δ" is memorized.

i) If the button 6g of the lever 6h is pressed, announcement is made, saying "Are the centers of the horizontal line and the vertical line overlapped? If overlapped, press the button 6g of the lever 6h. If the vertical line is on the upper side, tilt the lever 6h upward, and if on the lower side, tilt the lever 6h downward."

j) If the lever 6h is tilted upward, the right eye assumes BD prism and the left eye for BU prism, while if tilted downward, the right eye assumes the BU prism and the left eye for the BD prism.

k) Announcement is made, saying "Till the vertical line matches the center of the horizontal line, tilt the lever 6h upward or downward, and when matched, press the button 6g of the lever 6h."

l) Until the button 6g of the lever 6h is pressed, the number of times that the lever 6h is tilted upward or downward is counted. If the lever is tilted downward after being tilted upward, it makes 0 times on balance. The up is the right-eye hyperphoria, the down is the left-eye hyperphoria and the number of times being tilted in each direction x0.5 is a prism amount (Δ).

m) For the vertical heterophoria, "Right eye BD Δ" is memorized. Also, "Left eye BD Δ" is memorized.

(2) The cross heterophoria test is finished, and the landscape chart 99 is presented.

15. Stereoscopic vision test (1) Chart

FIG. 20 shows a test chart for stereoscopic vision, in which FIG. 20(a) shows a target 72A of the stereoscopic vision test chart for the left eye, FIG. 20(b) shows a target 72B of the stereoscopic vision test chart for the right eye, and FIG. 20(c) shows how the targets 72A and 72B are seen by both eyes with emmetropia.

In this stereoscopic test chart, fusion stimulation 72C is provided at the center of the test chart for the left eye, and fusion stimulation 72D is provided at the center of the test chart for the right eye.

The 4 straight lines of the target 72A and the target 72B have a staged stereoscopic parallax against the fusion stimulation 72C and the fusion stimulation 72D. For example, the stereoscopic parallax is 40" on the right side, 1' on the lower side, 2' on the upper side and 4' on the left side.

(2) How to measure a) The stereoscopic chart shown in FIG. 20 is presented.

b) Announcement is made, saying "Are the 4 straight lines seen like relief ? Tilt the lever 6h in the order from the highest relief. If they are not seen like relief, press the button 6g of the lever 6h."

c) If the button 6g of the lever 6h is pressed, "Stereoscopic: Requires close examination" is memorized and the test is finished.

d) If the lever 6h is tilted in the order of "left," "up," "down" and "right," "Stereoscopic: Normal" is memorized and the test is finished.

e) If the order is wrong, steps b) through d) are repeated and if a correct answer can not be gained, "Stereoscopic: Requires close examination" is memorized and the test is finished.

f) The landscape chart 99 is presented.

16. Binocular simultaneous objective refractive measurement for near targets (1) Convergence of the optometric apparatus body According to the PD distance, the optometric apparatus body is converted to a near setting distance d1 mm. A pitch angle of the optometric apparatus body (angle of convergence) θ can be obtained from the following equation:

$$\theta = \tan^{-1}((PD/2)/d1)$$

(2) Setting of near distance and angle of convergence a) The target illumination light source for both eyes is turned off.

b) A subjective measurement result for the far targets is set for both eyes.

Here, the subjective measurement result means "13. Selected refractivity selected at check of the optometric test results."

c) As a target, the landscape chart 99 or a target with the visual acuity value larger than the visual acuity value based on the S, C and Avalues of the subjective refractive measurement results (binocular balance) by 2 steps or 3 steps is presented to both eyes. In the case of a one letter target, a fusion frame is lighted.

d) The right and the left optometric apparatus bodies are rotated around the cycloduction point of the right and left eyeballs to be examined by the angle of convergence θ against the set near distance d1 mm.

e) The target light source for both eyes is lighted.

(3) Auto-alignment is carried out for both eyes at the same time.

(4) Announcement is made, saying "Please blink several times." After 1 second, announcement is made, saying "Please keep your eyes wide open and do not blink for some time," and "Tilt the lever 6h in the direction of the cut of the target."

(5) The response by the lever 6h and the direction of the cut in the target are determined, and if they match each other, go on to the next step.

(6) Binocular simultaneous objective measurement is carried out 3 times, for example.

(7) A difference between representative values of the S, C and A values of the measurement results of the objective measurement and the subjective refractive measurement value is outputted for display.

(8) How to understand the measurement results.

For example, if the binocular objective refractive measurement is carried out by setting the near distance d1 to 33 cm after the subjective refractive measurement for far targets, in the case of the eye to be examined with sufficient accommodation without accommodative functional disorder, the difference between the subjective refractive measurement value for the far target and the objective refractive measurement value measured by setting the near distance to 33 cm becomes 3D, regardless of abnormal refractivity of the examinee, and if the difference between the subjective refractive measurement value for the far target and the objective refractive measurement value by setting the near distance to 33 cm is 3D, it can be determined that the relation between accommodation and convergence is normal.

The accommodation degrades with age, and the value of a normal examinee is well known. Accommodation according to age is obtained objectively for near distance and compared with average accommodation for the age and if it is remarkably degraded, accommodative functional disorder can be suspected in the clinical ophthalmology. Also, from the viewpoint of prescription of spectacles for near distance, if the difference between the subjective refractive measurement value for the far targets and the objective refractivity value when set to the near distance 33 cm is 3D, it can be determined that the examinee have sufficient accommodation for the near distance 33 cm.

Spectacles for near distance are generally prescribed for examinees of 45 years old or above from the relation between accommodation and age, but by making binocular objective refractive measurement for near targets, whether spectacles for near distance are necessary or not can be objectively determined easily. Besides the above, this is effective for health management for VDT (video display terminal) workers.

Here, the accommodative functional disorder means lack of accommodation despite the young age.

Here, the position of a target is set to d1=33 cm from the position of a far distance while omitting the positions in the middle, but it is possible that the target is moved in steps from the position of a far distance toward the near distance d1 and stopped at the position after stepped movement and measurement operation (3) through (6) is carried out.

If the simultaneous objective measurement is executed by setting the target at the position of the near distance d1 form the position of the far distance while omitting the positions in the middle, targets can not be seen sometimes, but if measurement is made by moving the targets in steps in this way, accommodation is changed gradually, and accurate measurement can be made without losing the targets.

In the above, the difference between subjective refractive measurement value for the far target and the binocular objective refractive measurement target at a predetermined near distance is defined as accommodation, but the difference between the binocular objective refractive measurement value for the far targets and the binocular objective refractive measurement value at a predetermined near distance may be defined as accommodation.

17. Near distance test (1) Measurement of near distance dioptric power

Figure 21:
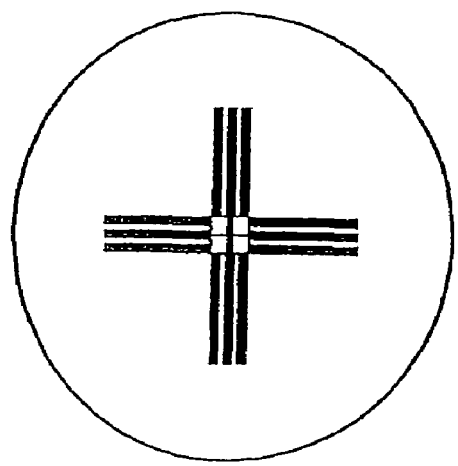
FIG. 21 is a view showing an example of a near chart.

The test chart for near distance shown in FIG. 21 is used.

Announcement is made, saying "Near distance test will be carried out. The near distance test will be explained."

(2) The near distance testing method is played with voice by movie.

a) The near distance test chart is explained.

b) Demonstration of "similarly clearly seen" and "the horizontal line is clear, but the vertical line is blurred," are played.

c) Explanation of lever operation is played by movie.

(3) Setting of angle of convergence a) The target illumination light source for both eyes is turned off.

b) The target shall be the near distance test chart shown in FIG. 21.

c) S and C are converted to the state where a cross cylinder of ±0.5D is added. The conversion formula is a publicly known formula.

d) While converging to the pitch angle 0 for the near distance d1 mm obtained in (1) convergence of the body, a near distance test initial value As according to the age obtained from the following formula is added to both eyes.

General formula of accommodation Ac for an age x

Under 55 years old: $Ac=12.5-0.2x$ 55 years old and above: $Ac=7.0-0.1x$

Addition power Ad1 for the near distance d1 mm $Ad1=(1000/d1)-(Ac)\times(1/2)$

A near distance test initial value As according to the age is added.

$As=-\{(1000/d1)-Ad1\}=-(Ac)\times(1/2)$

A calculation example of the near distance test initial value As according to the age is shown in Table 3 below.

TABLE 3

Calculation example of near distance test initial value As according to age

| Age x | Accommodation Ac | Initial value As |
|---|---|---|
| 40 | 4.5 | −2.25 |
| 42 | 4.1 | −2.05 |
| 45 | 3.5 | −1.75 |
| 48 | 2.9 | −1.45 |
| 50 | 2.5 | −1.25 |
| 52 | 2.1 | −1.05 |
| 55 | 1.5 | −0.75 |
| 60 | 1.0 | −0.50 |
| 65 | 0.5 | −0.25 | e) The target light source for both eyes is lighted.

(4) Announcement is made, saying "Near distance test will be made. Please hold the lever 6h and look into the optometric tester."

(5) Auto-alignment is executed for both eyes at the same time.

(6) Announcement is made, saying "Are the vertical line and the horizontal line seen equally thick? If they are seen equally thick, press the button 6g of the lever 6h. If the horizontal line is seen thick and the vertical line is seen thin, tilt the lever 6h to the right or left, and if the vertical line is seen thick and the horizontal line is seen thin, tilt the lever 6h to the front or back."

a) If the button 6g of the lever 6h is pressed at the first presentation (the horizontal line is seen as thick as the horizontal line.), a value obtained by adding (1000/d1) to Table 3. "Near distance test initial value As according to age" obtained in (4) d) shall be an addition power.

b) If the lever 6h is tilted to the left or right at the first presentation (the horizontal line is seen thick, and the vertical line is seen thin.), a spherical dioptric power +0.25D is added to both eyes at the same time.

c) Announcement is made, saying "Are the vertical line and the horizontal line seen equally thick? If they are seen equally thick, press the button 6g of the lever 6h. If the horizontal line is seen thick and the vertical line is seen thin, tilt the lever 6h to the left or right, and if the vertical line is seen thick and the horizontal line is seen thin, tilt the lever 6h to the front or back."

d) If the lever 6h is tilted to the left or right (the horizontal line is seen thick and the vertical line is seen thin.), a spherical dioptric power+0.25D is added to both eyes at the same time.

e) Announcement is made, saying "How about it?"

f) Until the button 6g of the lever 6h is pressed or the lever 6h is tilted to the front or back, the steps e) and f) are repeated.

g) When the button 6g is pressed or the lever 6h is tilted to the front or back, the sum of a value obtained by adding (1000/d1) to the value in Table 3 and a spherical dioptric power added till the button 6g of the lever 6h is pressed (the number of times that the button 6g of the lever 6h is pressed is counted) or tilted to the front or back (the number of times that the lever is tilted to the front or back is not counted) shall be the addition power, announcement is made, saying "Your near distance addition power is . . . D." and the near distance test is finished.

h) If the lever 6h is tilted to the front or back at the first presentation (the vertical line is seen thick and the horizontal line is seen thin), a spherical dioptric power of −0.25D is added to both eyes at the same time.

i) Announcement is made, saying "Are the vertical line and the horizontal line seen equally thick? If they are seen equally thick, press the button 6g of the lever 6h. If the horizontal line is seen thick and the vertical line is seen thin, tilt the lever 6h to the left or right, and if the vertical line is seen thick and the horizontal line is seen thin, tilt the lever 6h to the front or back."

j) If the lever 6h is tilted to the front or back (the vertical line is seen thick and the horizontal line is seen thin.), a spherical dioptric power −0.25D is added to both eyes at the same time.

k) Announcement is made, saying "How about it?"

l) Until the button 6g of the lever 6h is pressed or the lever 6h is tilted to the right or left, the steps k) and l) are repeated.

m) When the button 6g is pressed or the lever 6h is tilted to the right or left, the sum of a value obtained by adding (1000/d1) to the value in Table 3 and a spherical dioptric power added till the button 6g of the lever 6h is pressed (the number of times that the button 6g of the lever 6h is pressed is counted) or tilted to the right or left (the number of times that the lever is tilted to the right or left is counted) shall be the addition power, announcement is made, saying "Your distance addition power is . . . D." and the near distance test is finished.

n) The landscape chart 99 is presented to both eyes.

o) The near distance addition power is memorized.

p) S, C and A are converted to the state where ±0.5D cross cylinder lens is subtracted for both eyes.

18. Visual acuity for near distance test (1) Only when the near distance test has been carried out.

(2) Auto-alignment is carried out for both eyes at the same time.

Figure 22:
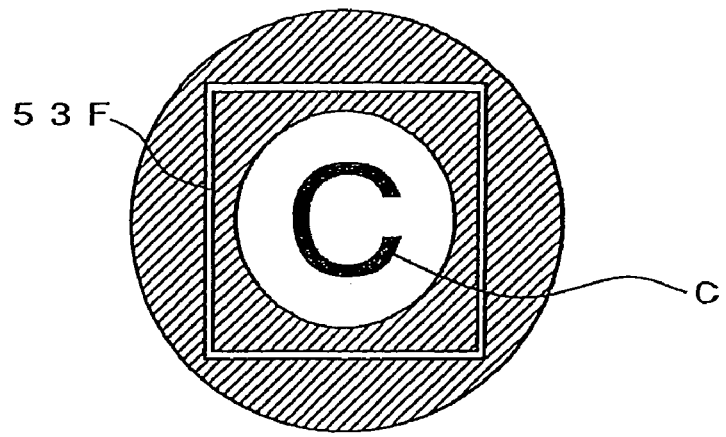
FIG. 22 is a view showing an example of a Landolt ring.

(3) Near visual acuity test for both eyes.

a) Announcement is made, saying "Near visual acuity test for both eyes is carried out."

b) The Landolt ring target 0.5 shown in FIG. 22 is set for both eyes. The fusion frame 53F is also presented at the same time.

c) Announcement is made, saying "Tilt the lever 6h in the direction of the cut of the target."

d) The customer tilts the lever 6h in the direction of the cut of the Landolt ring.

e) It is determined if the presented target matches the direction in which the lever 6h is tilted.

f) After determining the direction of the cut in the Landolt ring and the direction in which the lever 6h is tilted, the target of the next step is presented to both eyes at the same time.

g) Then, the steps of 5. Optometry when spectacles are worn (4) a) through (5) g) are followed.

h) The visual acuity value is memorized.

i) The landscape chart 99 is presented to both eyes.

19. An example of display of measurement results is shown in FIG. 29.

20. Measurement finished.

(1) With announcement saying "All the optometry has been finished," it is displayed in characters on the display screen 64q'.

(2) Then, announcement is made, saying "Remove your face from the apparatus and look at the monitor device 64q. The measurement results are displayed on the monitor device 64q'."

(3) The apparatus is set to be initialized.

a) PD shall be 66 mm. The target shall be the landscape chart 99 for both eyes.

b) The body shall be brought into the sleep state.

(Variation 1)

Figure 25:
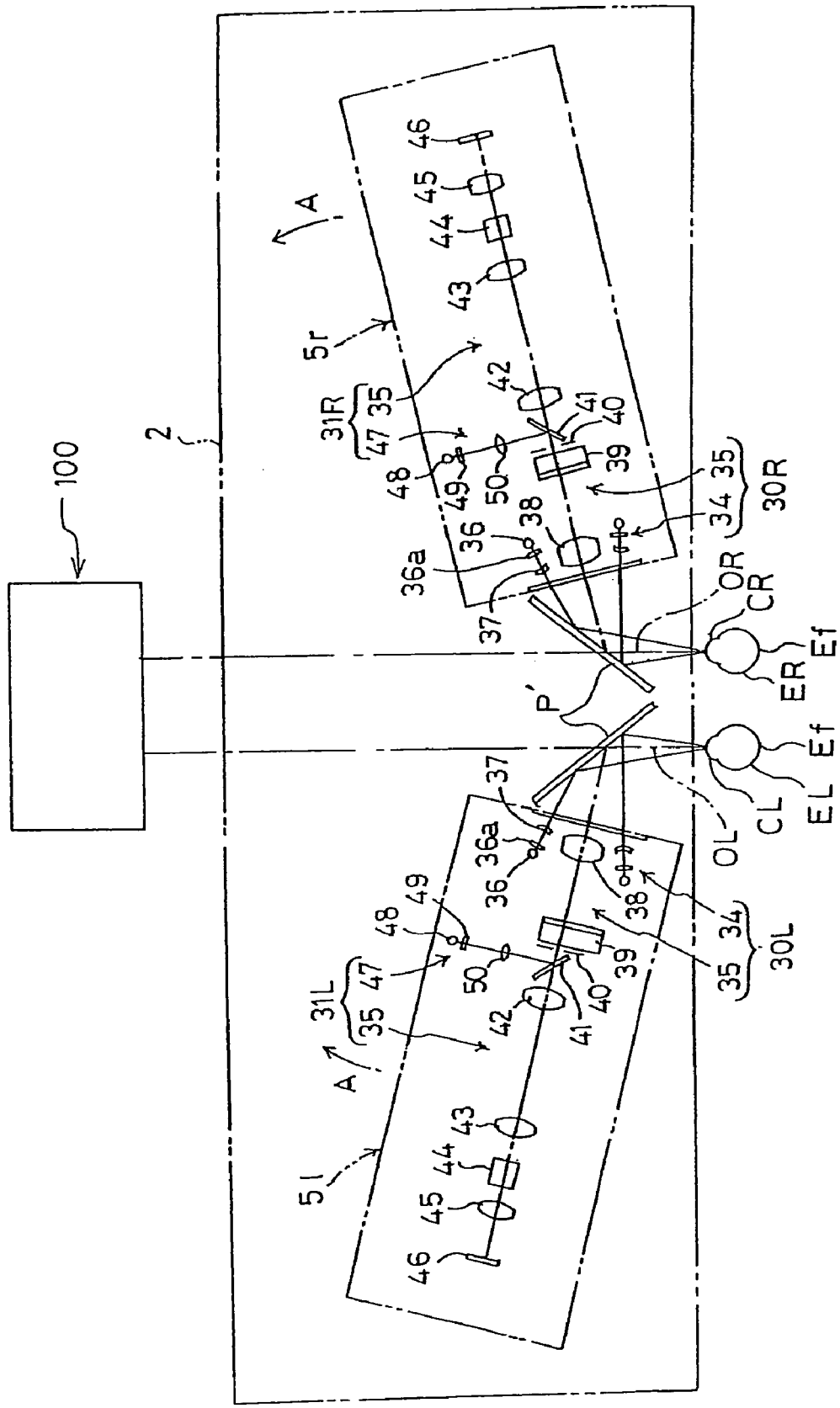
FIG. 25 is a view showing a variation of the optometric apparatus of the present invention and explanatory view with an optotypes device provided behind the optometric apparatus.

FIG. 25 is an explanatory diagram showing a variation of an optometric apparatus according to the present invention, and 100 refers to the optotypes examining device.

Figure 26:
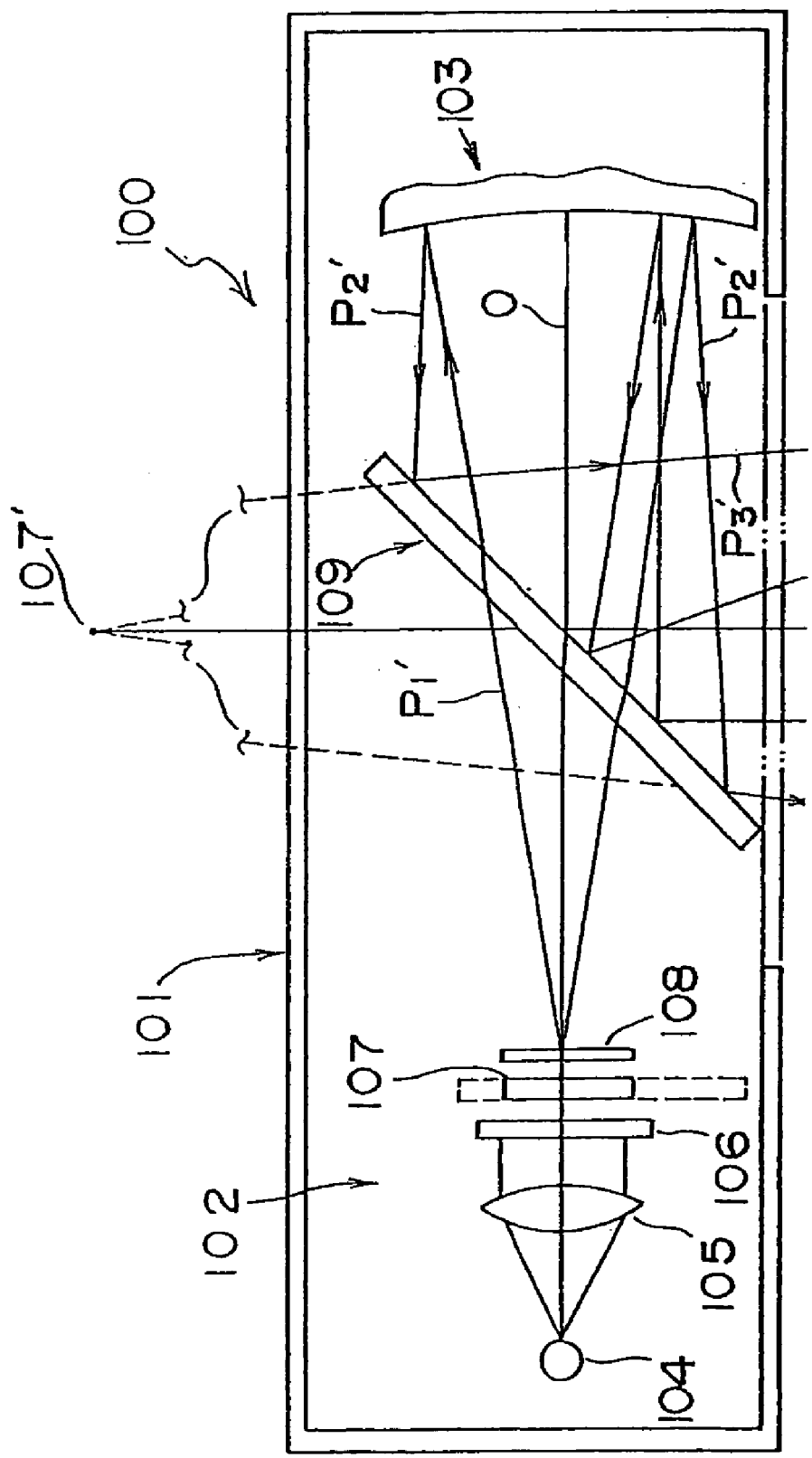
FIG. 26 is an explanatory view showing an internal constitution of the optotypes examining device.

This optotype examining device 100 has an enclosure 101 shown in FIG. 26, and the inside of this enclosure 101 is a camera obscura. In this enclosure 101, a target illumination optical system 102 and a concave mirror 103 are provided. In the target illumination optical system 102, a light source 104, a condenser lens 105, a diffusing plate 106, a target 107 and a polarizing plate 108 are provided. The diffusing plate 106 is used to soften illumination light, and the target 107 is illuminated through the diffusing plate 106. As the target 107, each of the above-mentioned targets is used. Into the target illumination optical system 102, the target 107 is selected and inserted. The polarizing plate 108 is provided in the neighborhood of the target 107. This polarizing plate 108 is inserted into the optical path of the target illumination optical system 102 at a binocular vision functional test.

Between the concave mirror 103 and the target illumination optical system 102, a semitransparent mirror 109 is arranged at an angle of 45 degrees to an optical axis O' of the illumination optical system 102. This semitransparent mirror 109 is formed by placing a dielectric film onto a parallel plane glass plate.

The target is transmitted through the semitransparent mirror 109 as shown by a symbol P1' and projected onto the concave mirror 103, reflected by this concave mirror 103 and oriented toward the semitransparent mirror 109 again as shown by a symbol P2', and by this semitransparent mirror 109, as shown by a symbol P3', projected in the direction where the right and the left mirrors P' exist, and through this mirror P', an image of the target is presented to the left eye and the right eye.

Figure 27:
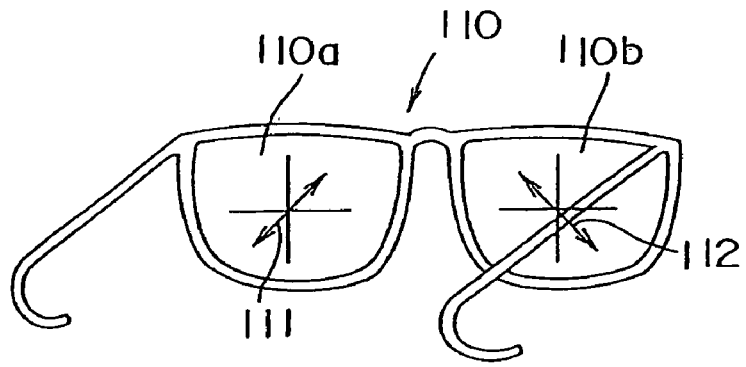
FIG. 27 is a perspective view showing an example of polarized glasses.
Figure 28:
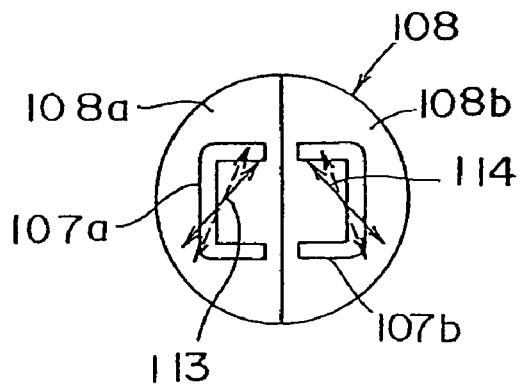
FIG. 28 is an explanatory view of a polarization axis of a polarization plate.

When binocular vision functional test is to be carried out, an examinee visually checks an image 107' by wearing polarized spectacles 110 shown in FIG. 27. A polarized lens 110a of the polarized spectacles 110 has a polarization axis 111 with the right 45 degrees, while the other polarized lens 110b has a polarization axis 112 of the left 45 degrees. Thus, as shown in FIG. 28, a polarization axis 113 of a half 108a corresponding to the polarized lens 110a of the polarizing plate 108 is designed with the right 45 degrees, a polarization axis 114 of 108b corresponding to the polarized lens 110b of the polarizing plate 108 is set to the right 45 degrees, an image of one of the targets can be seen by the left eye, and an image 107' of the target 107 can be seen by the right eye. The constitution of this optotypes device 100 is disclosed in the Japanese Patent Application No. 5-204402, for example.

(Variation 2)

Figure 31:
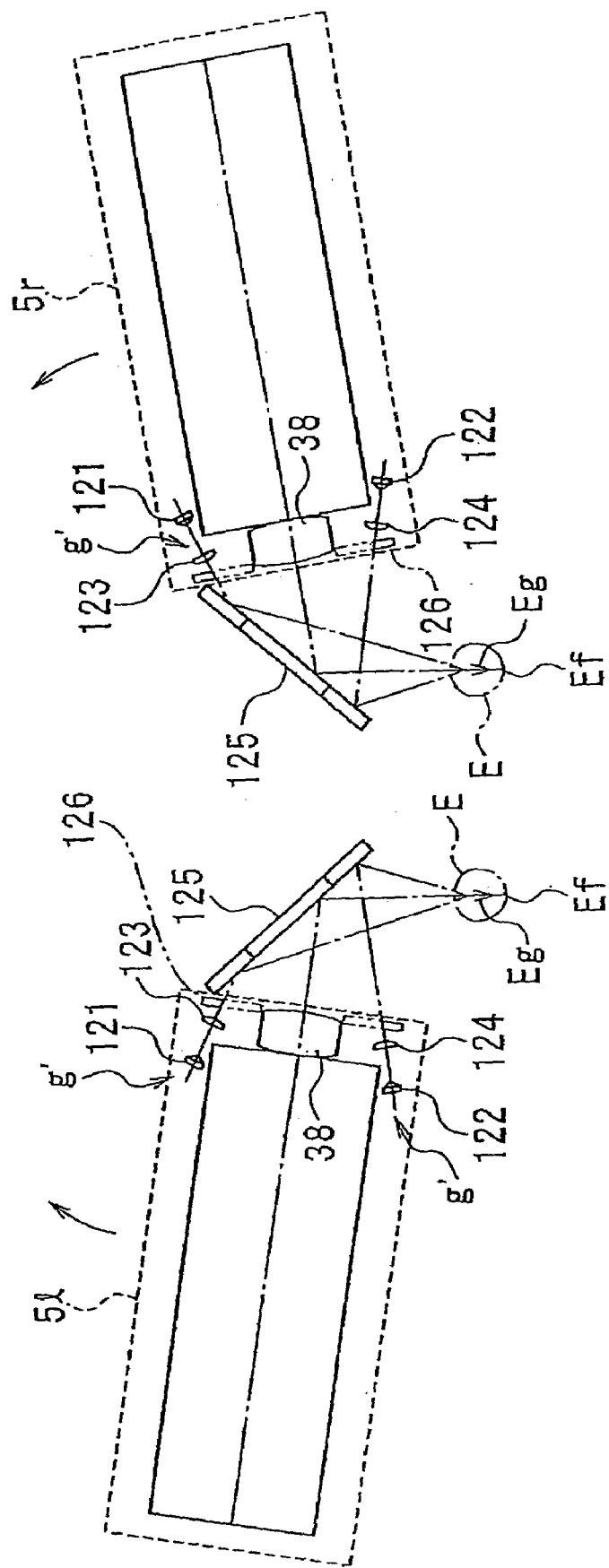
FIG. 31 is a block diagram showing an outline constitution of the optical system of a variation 2 of the optometric apparatus according to the present invention.
Figure 32:
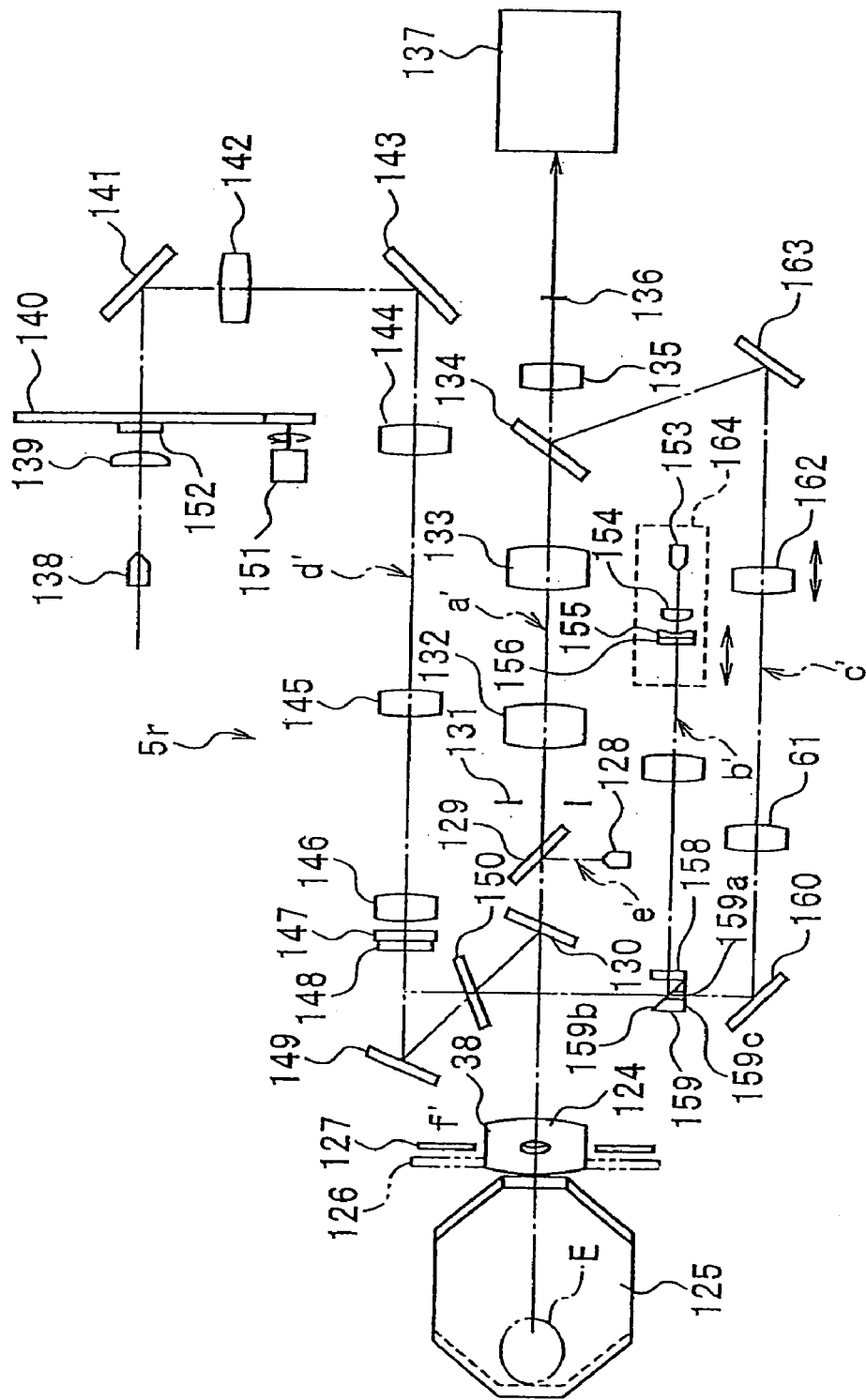
FIG. 32 is a view showing a detailed constitution of the optical system for the right eye shown in FIG. 31.

FIG. 31 is an explanatory diagram of a variation 2 of the optometric apparatus according to the present invention, in which an outline block diagram of the optical system for the right eye of the body portion 5r is shown, and FIG. 32 shows detailed constitution of the optical system for the right eye.

In this FIG. 31, 120 shows an optical system for the right eye of the body portion 5r. Since the constitution of an optical system for the left eye of the body portion 5l is the same as the optical system for the right eye, its explanation is omitted, and only the optical system 120 for the right eye will be described.

The optical system 120 for the right eye has, as shown in FIG. 31, a target projection optical system g' for distance matching between the eye E to be examined and the body portion 5r and a ring-pattern projection optical system f' for projecting a plurality of ring patterns toward the cornea of the eye E to be examined. This target projection optical system g' consists of, as shown in FIG. 31, LED 121 and 122 and projecting lenses 123 and 124.

A target light flux from the LED 121 and 122 of the target projection optical system g' is projected from two diagonal directions onto the cornea of the eye E to be examined through a mirror 125.

The ring-pattern projection optical system f' consists of, as shown in detail in FIG. 32, a ring-state illumination light source 127 and a ring pattern 126, and a concentric circular ring pattern image is projected similarly to the cornea of the eye E to be examined through the mirror 125. The ring-pattern projection optical system f' is also used as an anterior ocular segment illumination light source.

The optical system 120 for the right eye is provided with a light-receiving optical system a' for observation of the anterior ocular segment and alignment of the body portion 5r for the eye to be examined as well as measurement of corneal radius of curvature distribution, a target projection optical system b' for measurement of refractivity which projects a target for measuring the refractivity of the eye E to be examined to the fundus oculi Ef, a light-receiving optical system c' for receiving reflected light flux from the fundus oculi Ef, a target projection optical system d' for projecting a target for fixation and fogging vision of the eye E to be examined and a target projection optical system e' for projecting a target for alignment in the direction crossing the optical axis of the eye E to be examined and the objective lens 38 of the body portion 5r, that is, in the up-and-down and the right-and-left directions.

The target projection optical system e' is composed of a target LED 128 and a dichroic mirror 129. The target light flux from the target LED 128 is reflected by the dichroic mirror 129, transmitted through the dichroic mirror 130 and projected to the cornea of the eye E to be examined through the objective lens 38 and the mirror 125.

The light-receiving optical system a' has the objective lens 38, a dichroic mirror 130, a diaphragm 131, relay lenses 132 and 133, a dichroic mirror 134, an imaging lens 135 and an image pickup element 136. The diaphragm 131 is disposed at a focus position of the objective lens 38 and used as so-called telecentric diaphragm. A ray of light passing through the center of this diaphragm 131 is in parallel with the optical axis of the objective lens 38 on the eye to be examined.

Reflected light from the cornea by the target light flux from the target projection optical system e', diffused and reflected light from the cornea and the anterior ocular segment by the ring pattern 127 of the ring-pattern projection optical system f' and reflected light from the cornea by the target light flux from the target projection optical system g' are received by the image pickup element 136 through each optical element of the light-receiving optical system a'. The image receiving output of the image pickup element 136 is inputted to the monitor device 137.

The target projection optical system d' is provided with a lamp 138, a collimator lens 139, a rotating plate 140, a mirror 141, a relay lens 142, a mirror 143, a moving lens 144 for adjusting visibility of the eye to be examined, relay lenses 145 and 146, variable cross cylinders 147 and 148 for correction of astigmatism, a mirror 149 and a dichroic mirror 150.

The rotating plate 140 is rotated and driven by a motor 151, and a fixation marker, a Landolt ring, etc. are provided on the rotating plate 140.

The fixation marker 152 is projected to the eye E to be examined through the mirror 141, the relay lens 142, the mirror 143, the moving lens 144, the relay lenses 145 and 146, the variable cross cylinders 147 and 148, the dichroic mirrors 150 and 130, the objective lens 38 and the mirror 125.

By this, the eye E to be examined is fixed to the fixation marker 152, and the examiner carries out the anterior ocular segment observation of the eye E to be examined and alignment of the body portion 5r while watching the monitor device 137. In the state where the alignment is completed, curvature distribution of the cornea is measured first.

Since a ring pattern projected image of the ring pattern 126 formed on the cornea is imaged on the image pickup element 136 and a reflected luminescent spot image of the target light flux by the LED 128 is projected, by obtaining a distance to each of the ring images with this luminescent spot image as a reference on the image pickup element 136, the curvature distribution of the cornea can be obtained. It is also possible to obtain the corneal curvature distribution by calculating the distance from the center of a ring image with the smallest diameter of the concentric ring pattern images to each of the ring images.

The target projection optical system b' for measuring refractivity is comprised of a light source 153 for measuring ocular refractivity, a relay lens 154, a conical prism 155, a measurement ring target 156, a relay lens 157, a pupil ring diaphragm 158 and a triangular prism 159. The pupil ring diaphragm 158 is a ring-state diaphragm formed by etching on the lens. The pupil ring diaphragm 158 is disposed at a conjugation position with the pupil of the eye E to be examined.

When measurement of the corneal curvature distribution is finished, the light source 153 for measuring ocular refractivity is lighted and led to the relay lens 154, the conical prism 155, the measurement ring target 156, the relay lens 157, the pupil ring diaphragm 158 and the triangular prism 159, reflected by this triangular prism 159, the dichroic mirrors 150 and 130, led to the objective lens 38, transmitted through this objective lens 38, reflected by the mirror 125 and led to the pupil of the eye E to be examined. Since the pupil ring diaphragm 158 is conjugated with the pupil, the light flux emitted from the light source 153 for measuring ocular refractivity becomes a ring-state light flux on the pupil and projected to the fundus ocuh Ef as a measurement light flux.

The measurement light flux reflected by the findus oculi Ef of the eye E to be examined is led to the light-receiving optical system c' through the mirror 125, the objective lens 38, the dichroic mirrors 130 and 150 and the triangular prism 159.

The light-receiving optical system c' has a triangular prism 159, a mirror 160, a relay lens 161, a moving lens 162 and a mirror 163. The moving lens 162 is moved correspondingly to the refractivity of the eye E to be examined. The measurement light flux reflected by the fundus oculi Ef is transmitted through a center part 159a of the triangular prism 159, reflected by the mirror 160 and imaged on the image pickup element 136 through the relay lens 161, the moving lens 162, the mirror 163, the dichroic mirror 134 and the imaging lens 135. A reflecting surface 159b and a surface 159c on the opposite side of the triangular prism 159 are provided at a conjugation position with the pupil, and etching is given so that the reflection light flux from the findus oculi Ef emitted from the pupil passes only the central optical axis portion of the triangular prism 159.

The measurement light flux reflected by the findus oculi Ef is changed in the shape according to the refractivity of the eye E to be examined and imaged on the image pickup element 136. The refractivity of the eye E to be examined is obtained from the shape. Here, in order to improve measurement accuracy of the refractivity, a measurement light source unit 164, a moving lens 162 and the moving lens 144 are moved. This movement of the measurement light source unit 164 and the moving lens 162 is to bring the shape of the measurement reflected light flux from the findus oculi on the image pickup element 136 closer to the standard size. That is because the measurement accuracy is deteriorated if the image of the measurement reflected light flux formed on the image pickup element 136 is too small or too large. The measurement light source unit 164 is comprised of the light source 153 for measuring ocular refractivity, the relay lens 154, the conical prism 155 and the measurement ring target 156.

If this constitution is to be used, first, at the first measurement, the rough refractivity of the eye E to be examined is calculated and converted to a movement amount, the measurement light source unit 164 and the moving lens 162 are moved and measurement is made again. And at the second measurement, the value of ocular refractivity calculated based on the image of measurement reflected light flux formed on the image pickup element 136 and the refractivity obtained by the movement amount are added together to obtain the refractivity of the eye to be examined.

When this measurement of the objective refractivity for the eye to be examined is finished, a subjective optometry will be carried out.

The variable cross cylinders 147 and 148 are rotated around the optical axis according to the value of the refractivity, the moving lens 144 is moved along the optical axis, the rotating plate 152 is rotated, fixation markers required for subjective optometry, Landolt rings, for example, are set, the lamp 138 is lighted, and the fixation marker is presented to the eye E to be examined. And the subjective optometry is carried out. An example of the subjective examination is as previously explained.

And when the subjective examination to obtain far dioptric power is finished, an examination to obtain near dioptric power is carried out. As shown in FIG. 31, the body portions 5l and 5r are rotated around the center of cycloduction Eg of the eye E to be examined. The center of cycloduction Eg is, for example, a point on the side of the findus oculi by about 12 mm from the top of the cornea. Also, the fixation markers of the right and the left optical systems are set to the Landolt rings for measuring near dioptric power, and the variable cross cylinders 147 and 148 and the moving lens 144 are set so that they are the far dioptric power of the eye E to be examined.

Next, the moving lens 144 is moved to a position of, for example, the far dioptric power +(−1D), the body portions 5r and 51 are rotated around the center of cycloduction Eg so that the visual axes of both eyes accord to each other at the position of the far dioptric power +(−1D) and moved in the horizontal direction. Then, the lamp 138 is lighted, and the fixation marker is projected to the fundus oculi Ef of the right and the left eyes at the same time. By this, both of the eyes E to be examined are brought into the state the projected target is gazed.

At this time, in the same way as the objective measurement of far dioptric power, the light source 153 for measuring ocular refractivity is lighted so as to obtain the refractivity of both eyes E to be examined. When the eye E to be examined is correctly adjusted, a value with +(−1D) of the far dioptric power of the eye E to be examined should be obtained. That is because the set value of the far dioptric power +(−1D) is made to be gazed.

When the value of +(−1D) is obtained, the moving lens 144 is set to the position of +(−2D), and the body portions 5r and 51 are rotated around the center of cycloduction Eg so that the visual axes of both eyes accord to each other at the position of the far dioptric power +(−2D) and also moved in the horizontal direction. Next, the lamp 138 is lighted, and the both eyes E to be examined are made to gaze the projection target. And the refractivity of the both eyes E to be examined is obtained. If there is a difference between a value added to the far dioptric power and a measured value and the measured value is larger than the value obtained by addition, it is assumed that accommodation was not proper, and the near dioptric power is used as a value measured immediately before.

Figure 33:
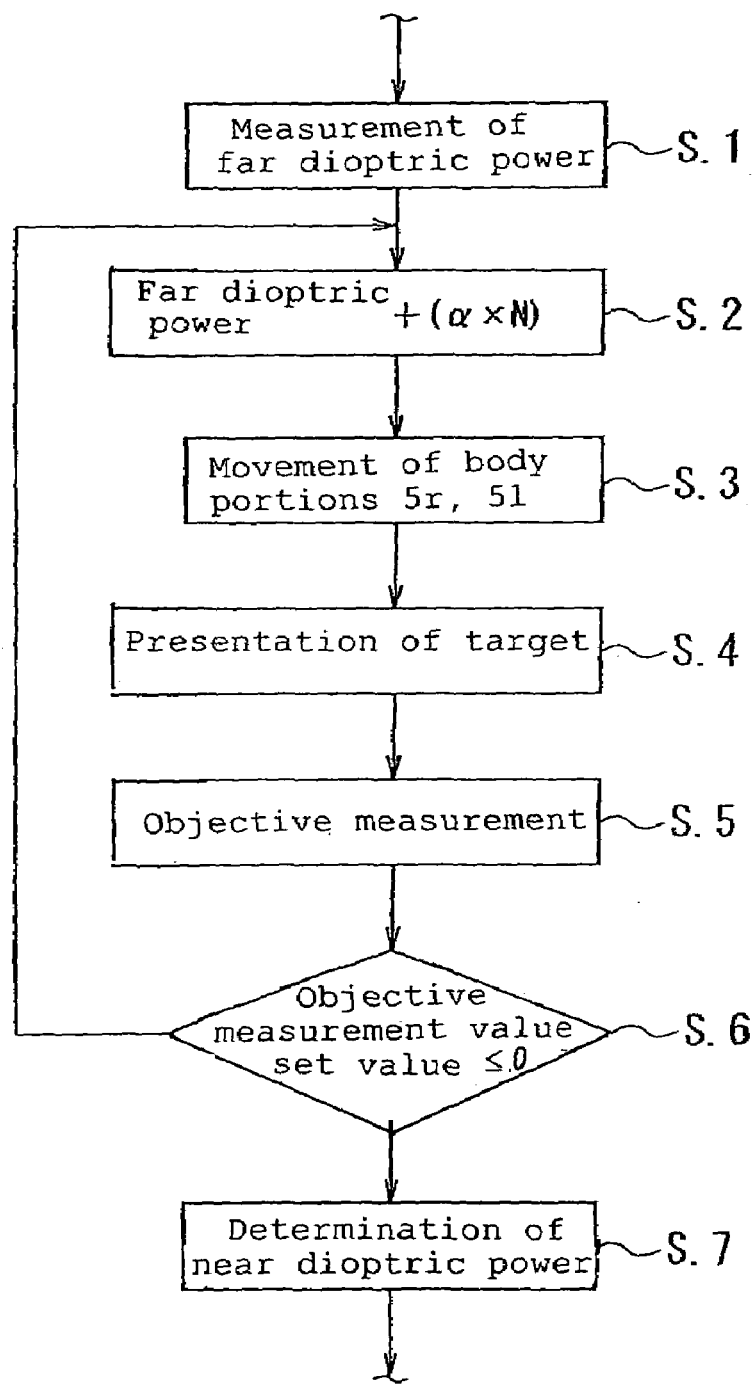
FIG. 33 is a flowchart for explaining action of the variation 2 of the optometric apparatus of the present invention.

That is, as shown in the flowchart in FIG. 33, the far dioptric power is measured (S. 1), a predetermined value a is added to the far dioptric power (S. 2), the body portions 5r and 51 are moved (S. 3), the target is presented (S. 4), the objective measurement is executed (S. 5), and if the difference between the measured value obtained by objective measurement and the set value is less than 0, the measurement is repeated in steps (S. 6), and the measurement is stopped when the difference becomes larger than 0 so as to determine the near dioptric power (S. 7).

The value of near dioptric power is, where the number of repeated steps is N:

Near dioptric power=Far dioptric power+α×(N−1)− Near position

For example, when α is (−1D), the near position is −3D, the far diptric power is 0D and the number of repeated steps is N=2, Near dioptric power=Far dioptric power+α×(N−1)− Near position=0+(−1)×1−(−3)=2

Therefore, according to this variation 2, the near dioptric power can be objectively measured for both eyes quantitatively and at the same time, not depending on the eye to be examined. Also, based on a response of the direction of the cut in the presented Landolt ring by tilting the lever 6h, it can be checked whether the eye E to be examined gazes the Landolt ring or not.

Also, if the objective measurement is carried out when the direction of the cut of the Landolt ring matches the direction where the lever 6h is tilted, the objective measurement can be made when the examinee is gazing, and measurement accuracy is improved.

Also, when the objective measurement is made several times and its average value is obtained, by presenting different Landolt rings such as Landolt rings with cuts in the different directions are presented to an examinee at every measurement, the accommodation state of the eye to be examined is maintained, and measurement accuracy is further improved.

INDUSTRIAL APPLICABILITY

According to the invention in claims 1 and 2, the examinee himself/herself can carry out optometry for both eyes at the same time.

According to the invention in claim 3, the success probability of auto-alignment for both eyes of the examinee for the optometric apparatus body can be improved.

According to the invention in claim 4, without hindering operation of the optometric apparatus by the examinee, an optometric assistant can check the operating state and give appropriate advice, which is convenient.

According to the invention in claim 5, without detailed explanation by optometrists or optometric assistants, the examinee can obtain how to operate the optometric apparatus.

According to the invention in claim 6, since comparison can be made between previous vision and the current vision, judgment can be made easily on whether new spectacles are required or not.

According to the invention in claims 7 through 11, the success probability of auto-alignment in a short time can be improved.

According to the invention in claim 12, without using a polarizing plate or polarized spectacles, binocular vision is enabled.

According to the invention in claim 13, accurate measurement is possible for examinees who have heterophoria but have no trouble in daily life.

According to the invention in claim 14, optometry using publicly known optotypes examining device can be made.

According to the invention in claims 16 and 17, relation between accommodation and convergence can be easily measured.

Especially, it has an effect that the near refractivity of an examinee can be measured quantitatively for both eyes at the same time without relying on response of the examinee.

The invention claimed is:

1. An optometric apparatus, comprising:
   optometric apparatus bodies each driven independently in fore-and-aft, right-and-left and up-and-down directions and each having a function to measure objective refraction and subjective refraction of a corresponding one of a right eye and a left eye of an examinee, for respective optometry of the examinee, provided on both sides of a face receiving device;
   a rotating mechanism provided for each of the optometric apparatus bodies and configured to rotate with a cycloduction point of the corresponding one of the right eye and the left eye of the examinee as a center;
   an auto-alignment mechanism provided in each of the optometric apparatus bodies and configured to automatically execute alignment for the corresponding one of the right eye and the left eye of the examinee; and
   a controller configured to set targets to a predetermined near distance after measurement by the subjective refraction for far targets is carried out, and configured to rotate the optometric apparatus bodies by the rotating mechanism with the cycloduction point of the right eye and the left eye as the center according to the predetermined near distance, so as to execute objective measurement of the right eye and the left eye.

2. The optometric apparatus according to claim 1, further comprising a monitor screen to present an image of an anterior ocular segment of at least one of the right eye and the left eye to an optometric assistant, provided at each of the optometric apparatus bodies.

3. The optometric apparatus according to claim 1, further comprising a monitor screen for explanation of optometry procedures by the examinee himself/herself through movie playing.

4. The optometric apparatus according to claim 3, wherein an image of an anterior ocular segment of at least one of the right eye and the left eye is presented on the monitor screen for explaining the optometry procedures by the examinee himself/herself by the movie playing.

5. The optometric apparatus according to claim 1, wherein comparison is made between a vision when recommended spectacles are worn and a vision with naked eyes or with dioptric power of currently used glasses.

6. The optometric apparatus according to claim 1, wherein the optometric apparatus is connected to a lens meter for measuring optical characteristics of a pair of spectacle lenses mounted to a spectacle frame, data of the optical characteristics of the spectacle lenses is inputted from the lens meter, and an initial value of PD value at auto-alignment is set based on the PD value as the optical characteristics data.

7. The optometric apparatus according to claim 6, wherein the lens meter measures the optical characteristics of the pair of spectacle lenses mounted to the spectacle frame at the same time.

8. The optometric apparatus according to claim 6, wherein the auto-alignment is carried out while maintaining the PD value.

9. The optometric apparatus according to claim 1, wherein an initial value of PD value is set according to at least one of age and sex of the examinee.

10. The optometric apparatus according to claim 1, wherein an initial setting of PD value is cancelled when alignment for one of the right eye and the left eye to be examined is gained, and data of the alignment is used as the alignment data for the other eye to be examined so that alignment of the other eye to be examined is automatically executed.

11. The optometric apparatus according to claim 1, further comprising an optical system configured to present targets for to the left eye, and an optical system configured to present targets for the right eye.

12. The optometric apparatus according to claim 11, further comprising a fusion target presenting optical system configured to present fusion targets at binocular optometry of the right eye and the left eye, provided in each of the optical systems.

13. The optometric apparatus according to claim 1, further comprising:
   a mirror opposing the left eye;
   a measurement optical system for objective measurement of the left eye;
   a mirror opposing the right eye;
   a measurement optical system for objective measurement of the right eye; and
   an optotypes examining device presenting optotypes from behind through the right mirror and the left mirror.

14. The optometric apparatus according to claim 1, wherein the controller is configured to calculate a difference between an objective refractive measurement value for the far targets and an objective refractive measurement value for the right eye and the left eye at the predetermined near distance, and a configured to determine accommodative functional disorder or necessity for the predetermined near distance based on a result of the calculation.

15. The optometric apparatus according to claim 14, wherein, when the controller sets the targets to the predetermined near distance, the controller is configured to execute step feeding of the targets so as to carry out the objective measurement for the right eye and the left eye at the same time in every time of execution of the step feeding.

16. The optometric apparatus according to claim 1, wherein, when the controller sets the targets to the predetermined near distance, the controller is configured to execute step feeding of the targets so as to carry out the objective measurement for the right eye and the left eye at the same time in every time of execution of the step feeding.

17. The optometric apparatus according to claim 1, wherein the targets include Landolt rings, and the controller is configured to instruct the examinee to tilt a lever in a direction of a cut in the Landolt ring, and configured to determine if a direction in which the lever is tilted matches the direction of the cut, to check whether the examinee is paying attention to the Landolt ring or not.

18. The optometric apparatus according to claim 17, wherein, when the direction in which the lever is tilted matches the direction of the cut in the Landolt ring, the controller is configured to start the objective measurement.

19. The optometric apparatus according to claim 18, wherein the controller is configured to present different Landolt rings to the examinee at every measurement if an average is to be obtained by executing the objective measurement several times.

* * * * *